United States Patent [19]
Smyser et al.

[11] Patent Number: 5,998,614
[45] Date of Patent: Dec. 7, 1999

[54] PREPARATION OF ASYMMETRIC CYCLIC UREAS USING AN ALKALI METAL IN LIQUID AMMONIA PROCESS

[75] Inventors: Thomas E Smyser, Wilmington; Pasquale N. Confalone, Greenville, both of Del.

[73] Assignee: DuPont Pharmaceuticals Company, Wilmington, Del.

[21] Appl. No.: 09/110,550

[22] Filed: Jul. 6, 1998

Related U.S. Application Data

[60] Provisional application No. 60/051,866, Jul. 7, 1997.
[51] Int. Cl.$^6$ .................................................. C07D 243/04
[52] U.S. Cl. ............................................... 540/492
[58] Field of Search ............................................... 540/492

[56] References Cited

U.S. PATENT DOCUMENTS

| | | | |
|---|---|---|---|
| 2,489,232 | 11/1949 | Goldberg et al. ........................ | 260/309 |
| 2,489,235 | 11/1949 | Goldberg et al. ........................ | 260/309 |
| 2,489,238 | 11/1949 | Goldberg et al. ........................ | 260/309 |
| 5,610,294 | 3/1997 | Lam et al. .............................. | 540/492 |
| 5,616,578 | 4/1997 | Otto ...................................... | 514/218 |
| 5,683,999 | 11/1997 | Jadhav et al. .......................... | 514/218 |

OTHER PUBLICATIONS

Bates et al., J. Org. Chem. (1986), 51(18), 3447–51.
Synth. Commun. (1991), 21(21), 2181–2187.
Hecht and Ohgi, (1981) J. Org. Chem. 46: pp. 1232–1234.
Weinreb et al. (1981) J. Org. Chem. 46:pp. 5383–5389.
Silverstein et al. (1986) Tetrahedron Letters, vol. 27, No. 41: pp. 4941–4944.
Field., (1978) J. Org. Chem., vol. 43, No. 6: pp. 1084–1085.
T. W. Greene, (1991) A Wiley–Interscience Publication, John Wiley & Sons, Inc., p. 401, "Protective Groups in Organic Synthesis."

*Primary Examiner*—Mukund J. Shah
*Assistant Examiner*—Bruck Kifle
*Attorney, Agent, or Firm*—Scott K. Larsen; Kenneth B. Rubin

[57] ABSTRACT

The present invention describes a method for the preparation of asymmetric N,N'-disubstituted cyclic ureas through the selective monodebenzylation of symmetric N,N'-disubstituted cyclic ureas using a dissolving metal reduction. The intermediates can be alkylated to give compounds which are useful as HIV protease inhibitors for the treatment of HIV infection.

20 Claims, No Drawings

PREPARATION OF ASYMMETRIC CYCLIC UREAS USING AN ALKALI METAL IN LIQUID AMMONIA PROCESS

This application claims the benefit of U.S. Provisional Application No. 60/051,866, filed Jul. 7, 1997.

FIELD OF THE INVENTION

The present invention describes a method for the preparation of asymmetric N,N'-disubstituted cyclic ureas through the selective monodebenzylation of symmetric N,N'-disubstituted cyclic ureas using a dissolving metal reduction. The intermediates can be alkylated to give compounds which are useful as HIV protease inhibitors for the treatment of HIV infection.

BACKGROUND OF THE INVENTION

The starting materials for the methods of the present invention are seven membered cyclic ureas containing C-2 symmetry. They have biological activity as human immunodeficiency virus (HIV) protease inhibitors. The asymmetric N,N'-disubstituted cyclic urea products of the methods of the present invention have also exhibited biological activity as human immunodeficiency virus (HIV) protease inhibitors for the treatment of HIV infection.

Debenzylation by the use of metals in liquid ammonia has been demonstrated on various substrates. The removal of O-benzyl protecting groups has been shown by Weinreb et al., *J. Org. Chem.*, 46, 5383 (1981), while removal of benzylated amides is reported in the following references: Hecht and Ohgi, *J. Org. Chem.*, 46, 1232 (1981); and Silverstein et al., *Tetrahedron Lett.*, 27, 4941 (1986). These disclosures however do not address the selective removal of a single benzyl protecting group from bisbenzylated substrates.

The monodebenzylation of N,N'-disubstituted cyclic ureas can be found in the synthesis of biotin reported by Field, *J. Org. Chem.*, 43, 1084 (1978), and Goldberg and Sternbach, U.S. Pat. Nos. 2,489,232 and 2,489,235 (issued Nov. 22, 1949). These references report removal of one N-benzyl protecting group from a bisbenzylated asymmetric cyclic urea with the stoichiometric use of sodium in liquid ammonia. The references teach that the debenzylation is governed by the alleviation of steric strain within the molecule. A method requiring a strict titration to a visual endpoint is described. The addition of the alkali metal to the solution containing the substrate in portions is used to achieve the desired amount of alkali metal. This approach requires the delicate addition of sodium and stipulates the use of precisely two equivalents of sodium. The only phenyl groups present in the biotin synthesis are those of the two N-benzyl protecting groups and under the conditions reported, overreduction was not a significant concern.

The process described herein involves symmetrical starting materials from which clean monodebenzylation would not be predicted. The selectivity cannot be attributed to alleviation of steric strain as in asymmetrical molecules. Additionally, the compounds of the present invention contain several benzyl groups present on carbon as well as nitrogen atoms wherein Birch reduction of the additional aromatic rings would be expected.

It was not previously appreciated that the amount of metal used is critical to obtaining a clean monodebenzylation product uncontaminated by starting material or completely debenzylated material. The present invention finds utility in the discovery that the use of excess sodium is not only permissable, but necessary for this class of compounds. This allows for the reverse addition of the substrate to the sodium ammonia mixture, eliminating the need for an undesirable titration with sodium on a large scale.

The order of addition described herein is desirable for large scale processes. The method calls for less handling of potentially harmful reactants because there is no need to accurately distribute elemental sodium. The substrate can be predissolved in a wide variety of co-solvents when the solubility in ammonia is low, and the reaction rate can easily be controlled by the flow rate of the addition solution which could prove critical considering the exothermic nature of the reaction.

Despite the conditions reported in the literature, the methods previously described are unattractive for a scalable process. There remains a need for a safe, viable and efficient process for the selective removal of benzyl protecting groups from symmetrical intermediates. These compounds can then be alkylated to give a wide range of unsymmetrical products which are useful as HIV protease inhibitors for the treatment of HIV infection.

SUMMARY OF THE INVENTION

The present invention concerns improved processes for the preparation of assymetric cyclic ureas. In the processes, a symmetric dibenzylated cyclic urea is selectively monodeprotected through the use of a dissolving metal reduction. The intermediates can be alkylated to give compounds which are useful as HIV protease inhibitors for the treatment of HIV infection. The invention allows for safer handling of alkali metal leading to the scalable preparation of a wide variety of assymmetrical cyclic ureas. The processes of the invention can be conducted on a kilogram scale, provide for high yields, and yield stable intermediates.

DETAILED DESCRIPTION OF THE INVENTION

In a first embodiment, the present invention provides a process for the preparation of compounds of formula (II):

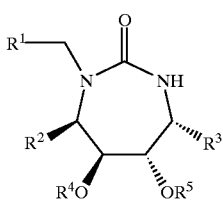

(II)

wherein:

$R^1$ is phenyl substituted with 0–3 $R^{1a}$;

$R^{1a}$ is selected from one or more of the following:
$C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —$NHSO_2R^{17a}$, —$NR^{16}R^{17}$, —$OR^{17}$, —$C(=O)NR^{16}R^{17}$, —$NR^{16}C(=O)R^{17a}$, —$OC(=O)NR^{16}R^{17}$, —$C(=O)R^{17a}$, —$NR^{16}CO_2R^{17a}$, —$SONR^{16}R^{17}$, and —$SO_2NR^{16}R^{17}$;

$R^{16}$ is independently hydrogen or $C_1$–$C_4$ alkyl;

$R^{17}$ is independently selected from:
hydrogen, $C_1$–$C_4$ alkyl, an amine protecting group when $R^{17}$ is bonded to N, and a hydroxyl protecting group when $R^{17}$ is bonded to O;

$R^{17a}$ is $C_1$–$C_4$ alkyl;

$R^2$ and $R^3$ are the same and individually selected from: benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl; and $R^4$ and $R^5$ are the same and individually a hydroxyl protecting group;

alternatively, $R^4$ and $R^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_2$CH$_2$CH$_2$CH$_3$)$_2$O—, —O—C(CH$_3$)(CH$_2$CH (CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

the process, comprising:

(1) contacting, at a suitable temperature for a sufficient amount of time, a solution of about 2.7 to about 4.4 equivalents of alkali metal dissolved in ammonia with about one equivalent of a compound of formula (I):

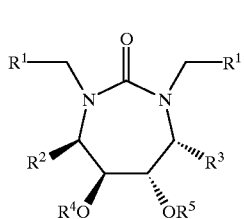

(I)

in an aprotic solvent;

(2) quenching the reaction of step (1) by addition of a suitable quenching agent to form a compound of formula (II); and (3) isolating the product.

In a more preferred embodiment, the present invention provides a process for the preparation of a compound of formula (II):

the process, comprising:

(1) contacting, at about −78° C. to about −33°C. for about 5 minutes to about 60 minutes, a solution of about 2.7 to about 4.4 equivalents of sodium metal dissolved in ammonia with about one equivalent of a compound of formula (I) in an aprotic solvent, selected from the group:
tetrahydrofuran, diethyl ether, ethylene glycol, dimethyl ether, t-butyl methyl ether, hexane, heptane, and cyclohexane;

(2) quenching the reaction of step (1) by addition of a suitable quenching agent, selected from the group: ammonium chloride, ammonium bromide and ammonium iodide;

to form a compound of formula (II); and (3) isolating the product.

In an even more preferred embodiment, the present invention provides a process for the preparation of a compound of formula (II-i):

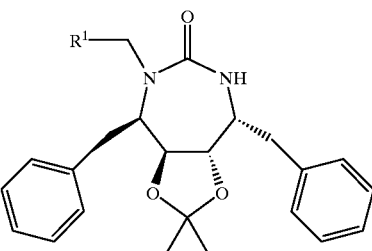

(II-i)

wherein:

$R^1$ is phenyl substituted with 0–2 $R^{1a}$;

$R^{1a}$ is selected from one or more of the following: $C_1$–$C_4$ alkyl, halogen, and —NR$^{16}$R$^{17}$;

$R^{16}$ is independently hydrogen or $C_1$–$C_4$ alkyl;

$R^{17}$ is independently selected from hydrogen, $C_1$–$C_4$ alkyl, and an amine protecting group;

said process comprising:

(1) contacting, at about −33° C. for about 15 minutes to about 60 minutes, a solution of about 2.9 to about 3.5 equivalents of sodium metal dissolved in ammonia with about one equivalent of a compound of formula (I-i):

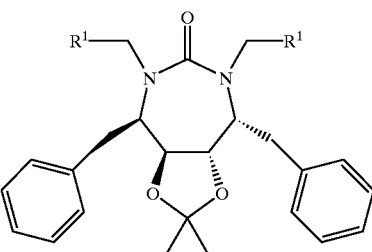

(I-i)

in an aprotic solvent solvent;

(2) quenching the reaction of step (1) by addition of ammonium chloride to form a compound of formula (II-i); and (3) isolating the product.

In a second embodiment, the present invention provides a process for the preparation of compounds of formula (III)

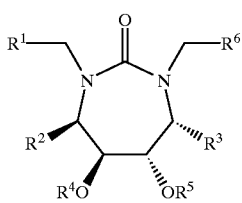

(III)

wherein:

$R^1$ is phenyl substituted with 0–3 $R^{1a}$;

$R^{1a}$ is selected from one or more of the following:
$C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —NHSO$_2$R$^{17a}$, —NR$^{16}$R$^{17}$,—OR$^{17}$, —C(=O)NR$^{16}$R$^{17}$, —NR$^{16}$C(=O)R$^{17a}$, —OC(=O)NR$^{16}$R$^{17}$, —C(=O)R$^{17a}$, —NR$^{16}$CO$_2$R$^{17a}$, —SONR$^{16}$R$^{17}$, and —S$_2$NR$^{16}$R$^{17}$;

R$^{16}$ is independently hydrogen or C$_1$–C$_4$ alkyl;

R$^{17}$ is independently selected from:
hydrogen, C$_1$–C$_4$ alkyl, an amine protecting group when R$^{17}$ is bonded to N, and a hydroxyl protecting group when R$^{17}$ is bonded to O;

R$^{17a}$ is C$_1$–C$_4$ alkyl;

R$^2$ and R$^3$ are the same and individually selected from: benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;

R$^4$ and R$^5$ are the same and individually a hydroxyl protecting group;

alternatively, R$^4$ and R$^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_3$CH$_2$CH$_2$CH$_3$)$_2$O—, —O—CH(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

R$^6$ is phenyl substituted with 0–3 R$^{6a}$;

R$^{6a}$ is selected from one or more of the following:
C$_1$–C$_8$ alkyl, C$_2$–C$_4$ alkenyl, C$_2$–C$_4$ alkynyl, C$_3$–C$_{10}$ cycloalkyl, C$_2$–C$_6$ alkoxyalkyl, C$_1$–C$_4$ haloalkyl, —NHSO$_2$R$^{19a}$, phenyl, —OH, halogen, azido, —CO$_2$R$^{19}$, cyano, —NR$^{18}$R$^{19}$, —OR$^{19}$, —NO$_2$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19}$, —OC(=O)R$^{19}$, —OCO$_2$R$^{19}$, and —NR$^{18}$CO$_2$R$^{19}$;

R$^{18}$ is independently selected from hydrogen and C$_1$–C$_4$ alkyl;

R$^{19}$ is independently selected from:
hydrogen, C$_1$–C$_4$ alkyl, phenyl, haloalkyl, an amine protecting group when R$^{19}$ is bonded to N, and a hydroxyl or carboxyl protecting group when R$^{19}$ is bonded to O; and R$^{19a}$ is C$_1$–C$_4$ alkyl;

said process comprising:

(1) contacting, at a suitable temperature for a sufficient amount of time, a solution of about 2.7 to about 4.4 equivalents of alkali metal dissolved in ammonia with about one equivalent of a compound of formula (I):

(I)

in an aprotic solvent;

(2) quenching the reaction of step (1) by addition of a suitable quenching agent to form a compound of formula (II)

(3) isolating a compound of formula (II); and (4) contacting a compound of formula (II) with at least one equivalent of a strong base and at least one equivalent a compound of formula (X):

$$Z^1\text{—CH}_2\text{—R}^6 \quad\quad\quad (X)$$

wherein:

Z$^1$ is chlorine, bromine, or iodine;

in a second aprotic solvent for a sufficient amount of time to effect formation of a compound of formula (III).

In a more preferred embodiment, the present invention provides a process for the preparation of a compound of formula (III);

the process, comprising:

(1) contacting, at about −78° C. to about −33° C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:
tetrahydrofuran, diethyl ether, ethylene glycol, dimethyl ether, t-butyl methyl ether, hexane, heptane, and cyclohexane;

(2) quenching the reaction of step (1) by addition of a suitable quenching agent, selected from the group:
ammonium chloride, ammonium bromide and ammonium iodide;

to form a compound of formula (II);

(3) isolating a compound of formula (II); and (4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;

and at least one equivalent a compound of formula (X) in a second aprotic solvent selected from the group:
tetrahydrofuran, diethyl ether, ethylene glycol, dimethyl ether, t-butyl methyl ether, toluene, benzene, xylene, hexane, heptane, and cyclohexane;

for a about 10 minutes to about 24 hours to effect formation of a compound of formula (III).

In an even more preferred embodiment, the present invention provides a process for the preparation of a compound of formula (III-i):

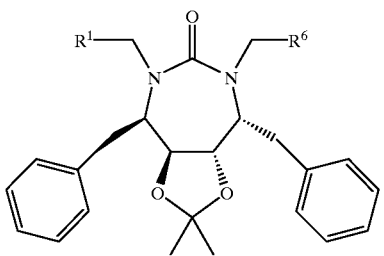

(III-i)

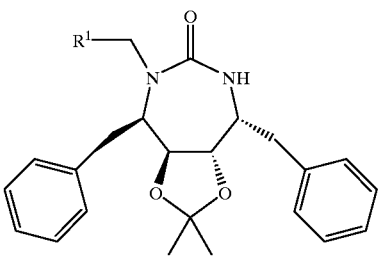

(II-i)

wherein:

$R^1$ is phenyl substituted with 0–2 $R^{1a}$;

$R^{1a}$ is selected from one or more of the following:
  $C_1$–$C_4$ alkyl, halogen, and —$NR^{16}R^{17}$;

$R^{16}$ is independently selected from hydrogen, $C_1$–$C_4$ alkyl, and an amine protecting group;

$R^{17}$ is independently selected from hydrogen, $C_1$–$C_4$ alkyl, and an amine protecting group;

$R^6$ is phenyl substituted with 0–2 $R^{6a}$;

$R^{6a}$ is selected from one or more of the following:
  $C_1$–$C_4$ alkyl, phenyl, —OH, halogen, —$CO_2R^{19}$, cyano, —$NR^{18}R^{19}$, —$OR^{19}$, —$NO_2$, —$C(=O)NR^{18}R^{19}$, —$NR^{18}C(=O)R^{19}$, —$OC(=O)NR^{18}R^{19}$, —$C(=O)R^{19}$, and —$OC(=O)R^{19}$;

$R^{18}$ is independently selected from hydrogen and $C_1$–$C_4$ alkyl; and $R^{19}$ is independently selected from:
  hydrogen, $C_1$–$C_4$ alkyl, phenyl, an amine protecting group when $R^{19}$ is bonded to N, a hydroxyl or carboxyl protecting group when $R^{19}$ is bonded to O; and said process comprising:

(1) contacting, at about −33° C. for about 15 minutes to about 60 minutes, a solution of about 2.9 to about 3.5 equivalents of sodium metal dissolved in ammonia with about one equivalent of a compound of formula (I-i):

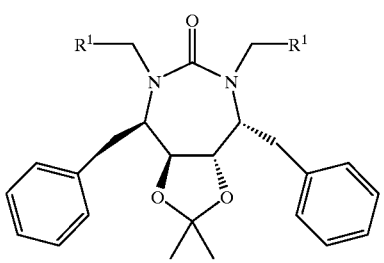

(I-i)

in an aprotic solvent;

(2) quenching the reaction of step (1) by addition of ammonium chloride to form a compound of formula (II-i);

(3) isolating a compound of formula (II-i); and (4) contacting a compound of formula (II-i) with at least one equivalent of potassium t-butoxide or sodium hydride and at least one equivalent a compound of formula (X):

$$Z^1—CH_2—R^6 \qquad (X)$$

wherein $Z^1$ is chlorine or bromine;

in a second aprotic for about 15 minutes to about 24 hours to effect formation of a compound of formula (III-i).

In a third embodiment, the present invention provides a process for the preparation of compounds of formula (IV)

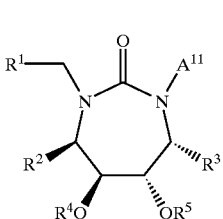

(IV)

wherein:

$R^1$ is phenyl substituted with 0–3 $R^{1a}$;

$R^{1a}$ is selected from one or more of the following:
  $C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —$NHSO_2R^{17a}$, —$NR^{16}R^{17}$, —$OR^{17}$, —$C(=O)NR^{16}R^{17}$, —$NR^{16}C(=O)R^{17a}$, —$OC(=O)NR^{16}R^{17}$, —$C(=O)R^{17a}$, —$NR^{16}CO_2R^{17a}$, —$SONR^{16}R^{17}$, and —$SO_2NR^{16}R^{17}$;

$R^{16}$ is independently hydrogen or $C_1$–$C_4$ alkyl;

$R^{17}$ is independently selected from:
  hydrogen, $C_1$–$C_4$ alkyl, an amine protecting group when $R^{17}$ is bonded to N, and a hydroxyl protecting group when $R^{17}$ is bonded to O;

$R^{17a}$ is $C_1$–$C_4$ alkyl;

$R^2$ and $R^3$ are the same and individually selected from:
  benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;

$R^4$ and $R^5$ are the same and individually a hydroxyl protecting group;

alternatively, $R^4$ and $R^5$ may be taken together along with the oxygen atoms to which they are attached to form a group selected from the group consisting of:
  —O—C(—$CH_2CH_2CH_2CH_2CH_2$—)—O—, —O—C($CH_2CH_3$)$_2$O—, —O—C($CH_3$)($CH_2CH_3$)—O—, —O—C(CH$_2$CH$_2$CH$_2$CH$_3$)$_2$O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

A$^{11}$ is C$_1$-C$_8$ alkyl substituted with 0–3 R$^{11}$;

R$^{11}$ is independently selected from the following:
C$_1$-C$_8$ alkyl, C$_2$-C$_4$ alkenyl, C$_2$-C$_4$ alkynyl, C$_3$-C$_{10}$ cycloalkyl, C$_2$-C$_6$ alkoxyalkyl, C$_1$-C$_4$ haloalkyl, —NHSO$_2$R$^{19a}$, phenyl, —OH, halogen, —NR$^{18}$R$^{19}$, —OR$^{19}$, —NO$_2$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19a}$, and —NR$^{18}$CO$_2$R$^{19}$;

R$^{18}$ is independently selected from hydrogen and C$_1$-C$_4$ alkyl;

R$^{19}$ is independently selected from:
hydrogen, C$_1$-C$_4$ alkyl, phenyl, haloalkyl, an amine protecting group when R$^{19}$ is bonded to N, and a hydroxyl or carboxyl protecting group when R$^{19}$ is bonded to O; and R$^{19a}$ is C$_1$-C$_4$ alkyl;

said process comprising:

(1) contacting, at a suitable temperature for a sufficient amount of time, a solution of about 2.7 to about 4.4 equivalents of alkali metal dissolved in ammonia with about one equivalent of a compound of formula (I):

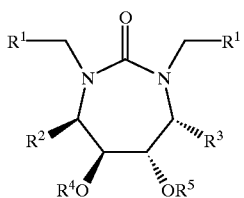

(I)

in an aprotic solvent;

(2) quenching the reaction of step (1) by addition of a suitable quenching agent to form a compound of formula (II);

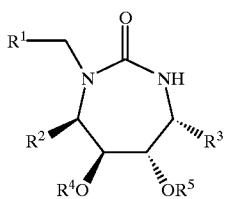

(II)

(3) isolating a compound of formula (II); and
(4) contacting a compound of formula (II) with at least one equivalent of a strong base and at least one equivalent a compound of formula (XI):

Z$^2$—A$^{11}$ (XI)

wherein Z$^2$ is chlorine, bromine, or iodine;
in a second aprotic solvent for a sufficient amount of time to effect formation of a compound of formula (IV).

In a more preferred embodiment, the present invention provides a process for the preparation of a compound of formula (IV):
the process, comprising:

(1) contacting, at about −78° C. to about −33° C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:
tetrahydrofuran, diethyl ether, ethylene glycol, dimethyl ether, t-butyl methyl ether, hexane, heptane, and cyclohexane;

(2) quenching the reaction of step (1) by addition of a suitable quenching agent, selected from the group:
ammonium chloride, ammonium bromide and ammonium iodide;

to form a compound of formula (II);

(3) isolating a compound of formula (II); and (4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;

and at least one equivalent a compound of formula (XI) in a second aprotic solvent selected from the group:
tetrahydrofuran, diethyl ether, ethylene glycol, dimethyl ether, t-butyl methyl ether, toluene, benzene, xylene, hexane, heptane, and cyclohexane; for a about 10 minutes to about 24 hours to effect formation of a compound of formula (IV).

In an even more preferred embodiment, the present invention provides a process for the preparation of a compound of formula (IV-i):

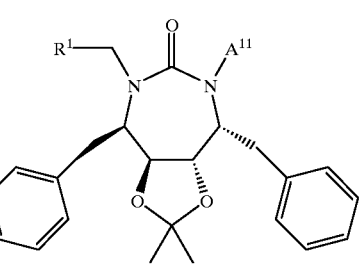

(IV-i)

wherein:
R$^1$ is phenyl substituted with 0–2 R$^{1a}$;

R$^{1a}$ is selected from one or more of the following:
C$_1$-C$_4$ alkyl, halogen, and —NR$^{16}$R$^{17}$;

R$^{16}$ is independently hydrogen or C$_1$-C$_4$ alkyl;

R$^{17}$ is independently selected from hydrogen, C$_1$-C$_4$ alkyl, and an amine protecting group;

A$^{11}$ is C$_1$-C$_4$ alkyl substituted with 0–3 R$^{11}$;

R$^{11}$ is independently selected from the following:
C$_1$-C$_4$ alkyl, C$_2$-C$_4$ alkenyl, C$_3$-C$_6$ cycloalkyl, C$_1$-C$_4$ haloalkyl, —NHSO$_2$R$^{19a}$, phenyl, halogen, —NR$^{18}$R$^{19}$, —OR$^{19}$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19a}$, and —NR$^{18}$CO$_2$R$^{19}$, R$^{18}$ is independently selected from hydrogen and C$_1$-C$_4$ alkyl; and R$^{19}$ is independently selected from:
hydrogen, C$_1$-C$_4$ alkyl, phenyl, an amine protecting group when R$^{19}$ is bonded to N, a hydroxyl or carboxyl protecting group when R$^{19}$ is bonded to O;

said process comprising:

(1) contacting, at about −33° C. for about 15 minutes to about 60 minutes, a solution of about 2.9 to about 3.5 equivalents of sodium metal dissolved in ammonia with about one equivalent of a compound of formula (I-i):

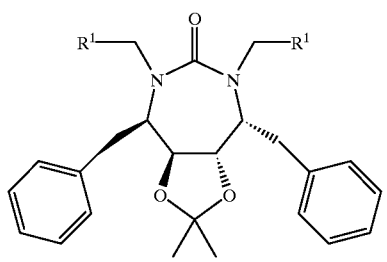

(I-i)

in an aprotic solvent;

(2) quenching the reaction of step (1) by addition of ammonium chloride to form a compound of formula (II-i);

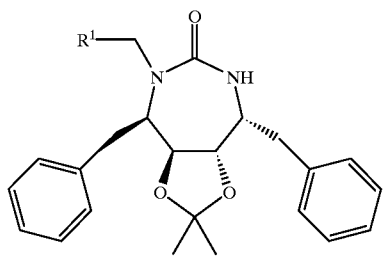

(II-i)

(3) isolating a compound of formula (II-i); and
(4) contacting a compound of formula (II-i) with at least one equivalent of potassium t-butoxide or sodium hydride and at least one equivalent a compound of formula (XI):

$Z^2$—$A^{11}$ (XI)

wherein $Z^2$ is chlorine or bromine;
in a second aprotic for about 15 minutes to about 24 hours to effect formation of a compound of formula (IV-i).

In a fourth embodiment, the present invention provides a process for the preparation of compounds of formula (VI)

(VI)

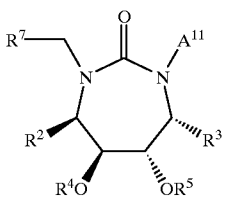

wherein:
$R^2$ and $R^3$ are the same and individually selected from:
benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;

$R^4$ and $R^5$ are the same and individually a hydroxyl protecting group;
alternatively, $R^4$ and $R^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_2$CH$_2$CH$_2$CH$_3$)$_2$O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

$R^7$ is phenyl substituted with 0–3 $R^{7a}$;
$R^{7a}$ is selected from one or more of the following:
$C_1$–$C_8$ alkyl, $C_2$–$C_4$ alkenyl, $C_2$–$C_4$ alkynyl, $C_3$–$C_{10}$ cycloalkyl, $C_2$–$C_6$ alkoxyalkyl, $C_1$–$C_4$ haloalkyl, —NHSO$_2$R$^{19a}$, phenyl, —OH, halogen, azido, —CO$_2$R$^{19}$, cyano, —NR$^{18}$R$^{19}$, —OR$^{19}$, —NO$_2$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19}$, —OC(=O)R$^{19}$, —OCO$_2$R$^{19}$, and —NR$^{18}$CO$_2$R$^{19}$;

$A^{11}$ is $C_1$–$C_8$ alkyl substituted with 0–3 $R^{11}$;
$R^{11}$ is independently selected from the following:
$C_1$–$C_8$ alkyl, $C_2$–$C_4$ alkenyl, $C_2$–$C_4$ alkynyl, $C_3$–$C_{10}$ cycloalkyl, $C_2$–$C_6$ alkoxyalkyl, $C_1$–$C_4$ haloalkyl, —NHSO$_2$R$^{19a}$, phenyl, —OH, halogen, —NR$^{18}$R$^{19}$, —OR$^{19}$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, C(=O)R$^{19a}$, and —NR$^{18}$CO$_2$R$^{19}$;

$R^{18}$ is independently selected from hydrogen and $C_1$–$C_4$ alkyl;
$R^{19}$ is independently selected from:
hydrogen, $C_1$–$C_4$ alkyl, phenyl, haloalkyl, an amine protecting group when $R^{19}$ is bonded to N, and a hydroxyl or carboxyl protecting group when $R^{19}$ is bonded to O; and
$R^{19a}$ is $C_1$–$C_4$ alkyl;

said process comprising:
(1) contacting, at a suitable temperature for a sufficient amount of time, a solution of about 2.7 to about 4.4 equivalents of alkali metal dissolved in ammonia with about one equivalent of a compound of formula (I):

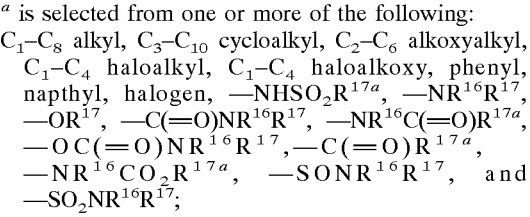

(I)

wherein:
$R^1$ is phenyl substituted with 0–3 $R^{1a}$;
$R^{1a}$ is selected from one or more of the following:
$C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —NHSO$_2$R$^{17a}$, —NR$^{16}$R$^{17}$, —OR$^{17}$, —C(=O)NR$^{16}$R$^{17}$, —NR$^{16}$C(=O)R$^{17a}$, —OC(=O)NR$^{16}$R$^{17}$, —C(=O)R$^{17a}$, —NR$^{16}$CO$_2$R$^{17a}$, —SONR$^{16}$R$^{17}$, and —SO$_2$NR$^{16}$R$^{17}$;
$R^{16}$ is independently hydrogen or $C_1$–$C_4$ alkyl;

$R^{17}$ is independently selected from:
hydrogen, $C_1$–$C_4$ alkyl, an amine protecting group when $R^{17}$ is bonded to N, and a hydroxyl protecting group when $R^{17}$ is bonded to O;

$R^{17a}$ is $C_1$–$C_4$ alkyl;

in an aprotic solvent;

(2) quenching the reaction of step (1) by addition of a suitable quenching agent to form a compound of formula (II);

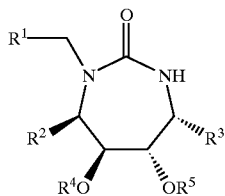

(II)

(3) isolating a compound of formula (II); and
(4) contacting a compound of formula (II) with at least one equivalent of a strong base and at least one equivalent a compound of formula (XI):

$$Z^2-A^{11} \qquad (XI)$$

wherein $Z^2$ is chlorine, bromine, or iodine;
in a second aprotic solvent for a sufficient amount of time to effect formation of a compound of formula (IV);

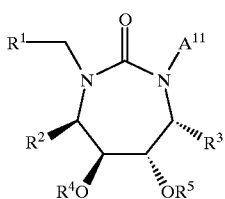

(IV)

(5) contacting, at a suitable temperature for a sufficient amout of time, a solution of about 2.7 to about 4.4 equivalents of alkali metal dissolved in ammonia with about one equivalent of a compound of formula (IV) in a third aprotic solvent;

(6) quenching the reaction of step (5) by addition of a suitable second quenching agent to form a compound of formula (V); and

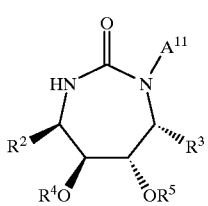

(V)

(7) isolating a compound of formula (V); and
(8) contacting a compound of formula (V) with at least one equivalent of a second strong base and at least one equivalent a compound of formula (XII), $$Z^3-CH_2-R^7 \qquad (XII)$$

wherein $Z^3$ is chlorine, bromine or iodine;
in fourth aprotic solvent for a sufficient amount of time to effect formation of a compound of formula (VI).

In a more preferred embodiment, the present invention provides a process for the preparation of a compound of formula (VI):

the process, comprising:
(1) contacting, at about $-78°$ C. to about $-33°$ C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:
tetrahydrofuran, diethyl ether, ethylene glycol, dimethyl ether, t-butyl methyl ether, hexane, heptane, and cyclohexane;

(2) quenching the reaction of step (1) by addition of a suitable quenching agent, selected from the group:
ammonium chloride, ammonium bromide and ammonium iodide;

to form a compound of formula (II);

(3) isolating a compound of formula (II); and
(4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;

and at least one equivalent a compound of formula (XI) in a second aprotic solvent selected from the group:
tetrahydrofuran, diethyl ether, ethylene glycol, dimethyl ether, t-butyl methyl ether, toluene, benzene, xylene, hexane, heptane, and cyclohexane;

for a about 10 minutes to about 24 hours to effect formation of a compound of formula (IV);

(5) contacting, at about $-78°$ C. to about $-33°$ C. for about 5 minutes to about 60 minutes, a solution of about 2.7 to about 4.4 equivalents of sodium metal dissolved in ammonia with about one equivalent of a compound of formula (IV) in a third aprotic solvent selected from the group:
tetrahydrofuran, diethyl ether, ethylene glycol, dimethyl ether, t-butyl methyl ether, hexane, heptane, and cyclohexane;

(6) quenching the reaction of step (5) by addition of a suitable second quenching agent, selected from the group:
ammonium chloride, ammonium bromide and ammonium iodide;

to form a compound of formula (V);

(7) isolating a compound of formula (V); and
(8) contacting a compound of formula (V) with at least one equivalent of a second strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;

and at least one equivalent a compound of formula (XII), in a fourth aprotic solvent selected from the group:
tetrahydrofuran, diethyl ether, ethylene glycol, dimethyl ether, t-butyl methyl ether, toluene, benzene, xylene, hexane, heptane, and cyclohexane;

for about 10 minutes to about 24 hours to effect formation of a compound of formula (VI).

In an even more preferred embodiment, the present invention provides a process for the preparation of a compound of formula (VI-i):

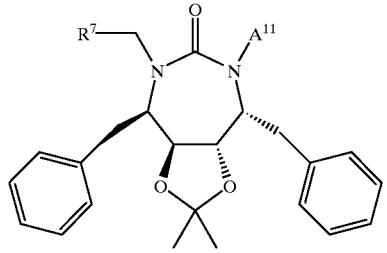

(VI-i)

wherein:

$R^7$ is phenyl substituted with 0–2 $R^{7a}$;

$R^{7a}$ is selected from one or more of the following:
$C_1$–$C_3$ alkyl, —OH, halogen, —$CO_2R^{19}$, cyano, —$NHR^{19}$, —$OR^{19}$, —$NO_2$, —C(=O)$NHR^{19}$, —NHC(=O)$R^{19}$, —OC(=O)$NHR^{19}$, —C(=O)$R^{19}$, and —OC(=O)$R^{19}$;

$A^{11}$ is $C_1$–$C_4$ alkyl substituted with 0–2 $R^{11}$, and $R^{11}$ is $C_1$–$C_2$ alkyl, $C_2$–$C_4$ alkenyl, halogen, —$NR^{18}R^{19}$ or —$OR^{19}$;

$R^{18}$ is independently selected from hydrogen and $C_1$–$C_4$ alkyl; and $R^{19}$ is independently selected from:
hydrogen, $C_1$–$C_3$ alkyl, an amine protecting group when $R^{19}$ is bonded to N, and a hydroxyl protecting group when $R^{19}$ is bonded to O;

said process comprising:

(1) contacting, at about –33° C. for about 15 minutes to about 60 minutes, a solution of about 2.9 to about 3.5 equivalents of sodium metal dissolved in ammonia with about one equivalent of a compound of formula (I-i):

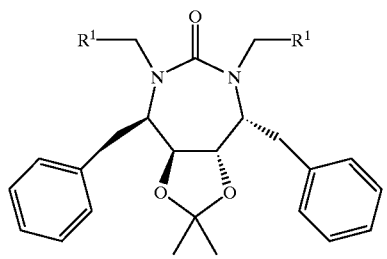

(I-i)

wherein:

$R^1$ is phenyl substituted with 0–2 $R^{1a}$;

$R^{1a}$ is selected from one or more of the following:
$C_1$–$C_4$ alkyl, halogen, and —$NR^{16}R^{17}$;

$R^{16}$ is independently hydrogen or $C_1$–$C_4$ alkyl;

$R^{17}$ is independently selected from hydrogen, $C_1$–$C_4$ alkyl, and an amine protecting group;

in an aprotic solvent;

(2) quenching the reaction of step (1) by addition of ammonium chloride to form a compound of formula (II-i);

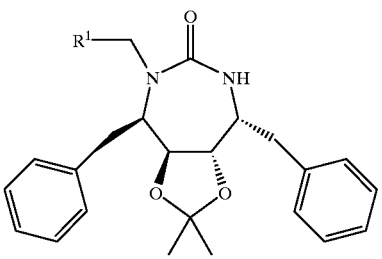

(II-i)

(3) isolating a compound of formula (II-i); and (4) contacting a compound of formula (II-i) with at least one equivalent of potassium t-butoxide or sodium hydride and at least one equivalent a compound of formula (XI):

$$Z^2—A^{11} \qquad (XI)$$

wherein $Z^2$ is chlorine or bromine;

in a second aprotic solvent for about 15 minutes to about 24 hours to effect formation of a compound of formula (IV-i):

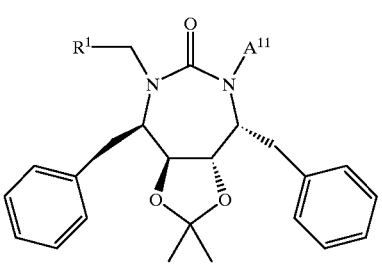

(IV-i)

(5) contacting, at about –33° C. for about 15 minutes to about 60 minutes, a solution of about 2.9 to about 3.5 equivalents of sodium metal dissolved in ammonia with about one equivalent of a compound of formula (IV-i) in a third aprotic solvent;

(6) quenching the reaction of step (5) by addition of ammonium chloride to form a compound of formula (V-i);

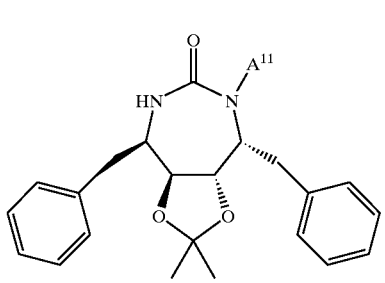

(V-i)

(7) isolating a compound of formula (V-i); and (8) contacting a compound of formula (V-i) with at least one equivalent of potassium t-butoxide and at least one equivalent a compound of formula (XII), $$Z^3—CH_2—R^7 \qquad (XII)$$

wherein $Z^3$ is chlorine or bromine;

in a fourth aprotic solvent for about 15 minutes to about 24 hours to effect formation of a compound of formula (VI-i).

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected. As used herein, the term "substrate" refers to the cyclic urea compound upon which chemical manipulation is to be performed, regardless of substitution.

As used herein, suitable aprotic solvents include, by way of example and without limitation, ether solvents and hydrocarbon solvents. Suitable ether solvents include tetrahydrofuran, diethyl ether, diethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether. Suitable hydrocarbon solvents include: butane, pentane, hexane, heptane, octane, nonane, decane, cyclohexane, cycloheptane, methylcyclohexane; as well as aryl hydrocarbon solvents.

As used herein, suitable acetate solvents include methyl, ethyl, propyl and iso-propyl acetate.

As used herein, suitable halogenated solvents include, but are not limited to chlorobutane, methylene chloride, chloroform, dichloroethane, carbon tetrachloride.

As used herein, suitable aryl solvents include toluene, benzene, o-xylene, m-xylene and p-xylene.

As used herein, the term "strong base" refers to any agent which effects the deprotonation of the urea nitrogen (alpha nitrogen to the urea carbonyl). Examples of such strong bases include, but are not limited to, alkoxides, alkyllithiums, metal amides, metal hydrides, metal dialkylamides and arylamines, wherein; alkoxides include lithium, sodium and potassium salts of methyl, ethyl and t-butyl oxides; alkyllithiums include, isobutyllithium, n-hexyllithium, n-octyllithium, n-butyllithium, s-butyllithium, t-butyllithium, phenyllithium and triphenylmethyllithium; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

As used herein, the term "quenching agent" refers to any agent which effects neutralization of a nitrogen anion by providing a proton and which is inert to reaction with the anion itself. Examples of quenching agents include, but are not limited to, ammonium salts, acids and water; wherein examples of such include ammonium chloride, ammonium bromide, ammonium sulfate, ammonium acetate, ammonium phosphate, ammonium tartrate, acetic acid, propionic acid, butanoic acid, tartaric acid, hydrobromic acid, hydrochloric acid, phosphoric acid and sulfuric acid.

As used herein, "alkyl" is intended to include both branched and straight chain saturated aliphatic hydrocarbon groups having one to twelve carbon atoms; for example, $C_1$–$C_4$ alkyl includes methyl ethyl, n-propyl, i-propyl, n-butyl, i-butyl, s-butyl, and t-butyl. "Alkenyl" is intended to include hydrocarbon chains of either a straight or branched configuration and one or more unsaturated carbon-carbon bonds which may occur in any stable point along the chain, such as ethenyl, 1-propenyl, 2-propenyl, 1-butenyl, 2-butenyl, 3-butenyl, 1,3-butadienyl and the like; and "alkynyl" is intended to include hydrocarbon chains of either a straight or branched configuration and one or more triple carbon-carbon bonds which may occur in any stable point along the chain, such as ethynyl, propynyl, butynyl and the like.

As used herein, "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl.

As used herein "halo" or "halogen" refers to fluoro, chloro, bromo and iodo.

As used herein "haloalkyl" is intended to include both branched and straight-chain saturated aliphatic hydrocarbon groups having the specified number of carbon atoms, substituted with 1 or more halogen.

As used herein "alkoxyalkyl" represents an alkyl group of indicated number of carbon atoms attached through an oxygen bridge. For example $C_1$–$C_4$ alkoxyalkyl includes methoxy, ethoxy, propoxy and butoxy.

As used herein "alkylcarbonyl" is intended to include an alkyl group of an indicated number of carbon atoms attached through a carbonyl group to the residue of the compound at the designated location.

As used herein "alkylcarbonyloxy" is intended to include an alkyl group of an indicated number of carbon atoms attached to a carbonyl group, where the carbonyl group is attached through an oxygen atom to the residue of the compound at the designated location.

As used herein, the term "hydroxyl protecting group" (or "O-protected") refers to any group known in the art of organic synthesis for the protection of hydroxyl groups stable to the reaction conditions used. Protecting groups are base-stable and can include, but are not limited to ether types and alkyl types. Exemplary are methyl, methoxymethyl (MOM), t-butoxymethyl, 2-methoxyethoxymethyl (MEM), tetrahydropyranyl ether (THP), 4-methoxytetrahydro pyranyl ether, 4-methoxytetrahydrothiopyranyl ether, tetrahydrofuranyl ether, 1-ethoxyethyl ether, 1-methyl-1-methoxyethyl ether, t-butyl ether, isopropyldimethyl-silyl ether, t-butyldimethylsilyl ether (TBDMS), t-butyldiphenylsilyl ether, triisopropylsilyl ether.

As used herein, the term "amine protecting group" (or "N-protected") refers to any group known in the art of organic synthesis for the protection of amine groups which are stable to the reaction conditions used. Examples of amine protecting groups include, but are not limited to, the following; methyl carbamate, 2-trimethyl silylethyl carbamate, t-butyl carbamate (Boc), cyclobutyl carbamate, 1-methylcyclobutyl carbamate, 1-adamantyl carbamate, vinyl carbamate, allyl carbamate, N-methoxymethyl and N-tetrahydropyranyl.

As used herein, suitable recrystallization solvents include those with a boiling point lower than the melting point of the product, in which the product will dissolve when heated and crystallize when cooled. Examples include, but are not limited to alkanes, ethers, acetates, alcohols, halogenated alkanes, organic acids and water.

When any variable (for example, $R^{1a}$, $R^{6a}$, p, etc.) occurs more than one time in any constituent or formula for a compound, its definition on each occurrence is independent of its definition at every other occurrence. Thus, for example, if a group is shown to be substituted with 0–3 $R^{1a}$, then said group may optionally be substituted with up to three $R^{1a}$ and $R^{1a}$ at each occurrence is selected independently from the defined list of possible $R^{1a}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —C($R^{1a}$)$_2$—, each of the two $R^{1a}$ substituents on C is independently selected from the defined list of possible $R^{1a}$.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The following terms and abbreviations are used herein and defined as follows. The abbreviation: "THF" as used herein means tetrahydrofuran, "HPLC" as used herein means high performance liquid chromatograpy, "TLC" as used herein means thin layer chromatography, "liq" as used herein means liquid, and "t-BuOK" as used herein means potassium tert-butoxide.

The methods of the present invention, by way of example and without limitation, may be further understood by reference to Scheme 1. Scheme 1 details the general synthetic method for monodebenzylation of symmetrical cyclic ureas and subsequent alkylation to give asymmetric products. In Scheme 1, $R^1$, $R^6$ and $R^7$ are substituted or unsubstituted phenyl groups; $R^2$ and $R^3$ are substituted or unsubstituted benzyl groups; and $A^{11}$ and $A^{12}$ are substituted or unsubstituted alkyl groups.

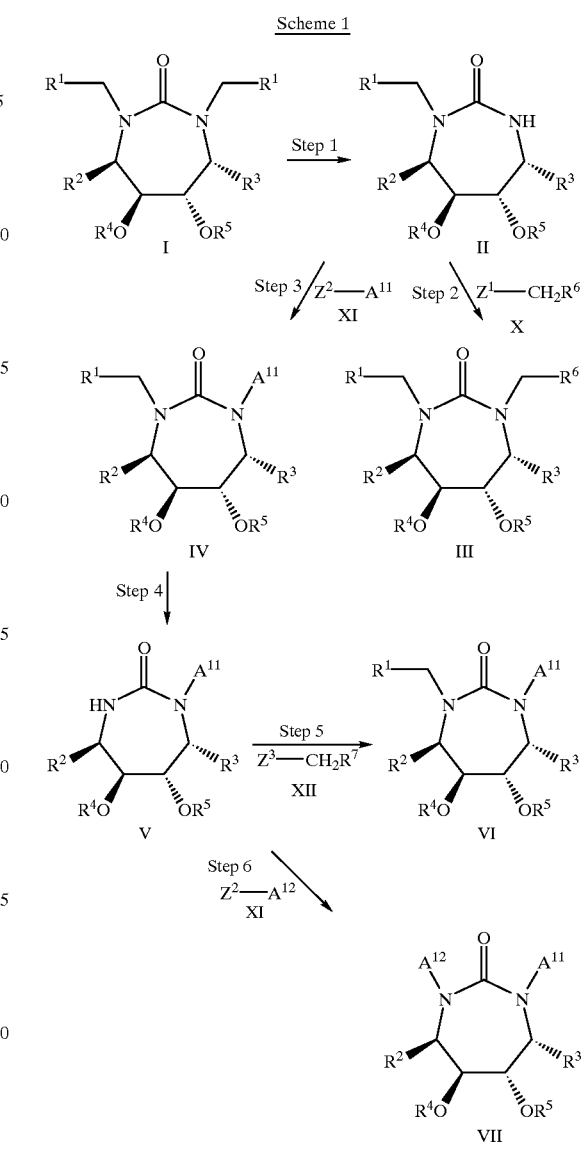

Scheme 1

The reaction carried out in Step 1 has been run on various scales up to 0.3 mole in kilo laboratory glassware.

In Step 1, the vessel is purged with argon or nitrogen to provide an inert atmosphere. The solvent for the reaction is charged into the vessel and cooled to a low temperature. Acceptable solvents include, but are not limited to low molecular weight amines such as liquid ammonia, dimethyl amine, trimethyl amine. The most preferred is liquid ammonia. It is also possible to reduce the amount of ammonia by use of additives such as naphthalene (anthracene or benzophenone) to form the metal naphthalide with solubility in ether solvents. The possible temperature range is from about −78° C. to about 25° C. The preferred range is about −78° C. to about −33° C. The most preferred is about −33° C. which is consistent with the boiling point of the liquid ammonia. The solution is kept at a constant temperature by the use of a dry ice/acetone bath or constant temperature apparatus as necessary. While it is possible to run Step 1 at lower temperatures, it may have the affect of extending reaction time which is readily understood by one skilled in the art.

The alkali metal is added to the reaction pot once a suitable temperature is achieved wherein the alkali metal is chosen from either sodium, lithium or potassium. The most preferred is sodium. The metal should be added at a rate which will not largely affect pot temperature. The solution turns blue upon addition of the metal. The amount of metal used to carry out the removal of the benzyl group is critical. The possible range of molar equivalents is about 2.7 to about 4.0. Most preferred is about 2.9 to about 3.3. If the substrate contains acidic protons, one extra equivalent of metal should be used for each proton removable under the conditions. If too small an amount of alkali metal is used, the product will be contaminated with unchanged starting material. If too large an amount of alkali metal is used the product will be contaminated with completely debenzylated by-product.

The substrate is charged to the vessel after being dissolved in a suitable aprotic solvent. Preferred aprotic solvents include ethers and hydrocarbons. The most preferred is tetrahydrofuran. Enough solvent should be used to completely solubilize the substrate while maintaining the best solvent efficiency possible. An acceptable range is about 3 mL to about 15 mL of solvent per gram of starting material. The most preferred is about 5 mL per gram. The rate of addition should be consistent with maintaining the desired pot temperature and will be scale dependent. The addition can be performed at variety of rates but it is preferred that the addition take from about fifteen minutes to about one hour. Most preferred is about 30 minutes.

The solution is allowed to stir for about 0.5 hours to about 1 hour after the substrate is added, at which time the progress of the debenzylation can be monitored by HPLC or TLC analysis of reaction aliquots quenched with acidic eluant. The reaction, after a sufficient amount of time, is considered complete when the dibenzylated starting material has been completely consumed. Typical reaction times range from 10 minutes to 1 hour. The preferred reaction time will involve quenching immediately after the starting material is consumed.

The reaction is quenched with an excess of suitable quenching agent at reduced temperature. Although a wide range of suitable quenching agents are possible, ammonium salts are preferred of which ammonium chloride is most preferred. Any remaining blue solution color disappears upon quenching. The possiblity for extreme exotherms exists due to the reaction of any residual sodium with the quenching agent, and any precautions necessary will be readily understood by one skilled in the art. After addition of the quenching agent, the solution is warmed to room temperature and the vessel is swept with a stream of inert gas for several hours to remove the gaseous ammonia.

The remaining contents of the vessel are partitioned between organic and aqueous phases. Acceptable organic solvents include any low boiling, water immiscible solvents in which the product is soluble. Preferred solvents include ethers, acetates, aryls and chlorinated hydrocarbons. The most preferred is ethyl acetate. The aqueous phases are extracted repeatedly with the chosen organic solvent. The combined organics are washed with water, subjected to a drying agent and stripped under vacuum. The resulting residue can then be recrystallized from a suitable recrystallization solvent to give a compound of formula II. Appropriate solvent choice for recrystallization is compound dependent and readily understood by one skilled in the art.

In Step 2, the compound obtained from Step 1 is dissolved in about 5 mL to about 10 mL per gram of a suitable aprotic solvent and then cooled to 0° C. for base addition. The preferred solvents include, but are not limited to ethers, cyclic ethers, aryls, hydrocarbons, chlorinated hydrocarbons. The most preferred is tetrahydrofuran. The urea is deprotonated by the addition of about 1.0 to 1.5 equivalents of a strong base. Although a wide range of bases are possible, alkoxides, metal hydrides and metal amides are preferred. Potassium tert-butoxide is most preferred. The solution is stirred for about 0.25 hours to about 0.5 hours followed by the addition of a benzylhalide electrophile of formula (X) dissolved in 0 mL to 10 mL per gram of reaction solvent. The resulting mixture is then stirred for several hours at temperatures ranging from about 0° C. to about 80° C. The preferred range is about 25° C. to about 65° C. The alkylation is monitored by HPLC or TLC after quenching with acidic eluant. The reaction is considered complete when the complete consumption of starting material is observed.

The suspension is quenched with a suitable quenching agent and partitioned between an organic phase and water. Acceptable organic solvents include any low boiling, water immiscible solvents in which the product is soluble. Preferred solvents include ethers, acetates, aryls and chlorinated hydrocarbons. The most preferred is ethyl acetate. The aqueous phase is extracted repeatedly organic solvent and the combined organic layers are washed with water and brine, dried over sodium sulfate and the solvent removed under vacuum. The resulting residue can then be recrystallized from a suitable recrystallization solvent to give a compound of formula III. Appropriate solvents for recrystallization will be compound dependent and are readily understood by one skilled in the art.

In Step 3, a compound of formula (II) is subject to the urea anion formation described above in Step 2, afterwhich an alkylhalide of the formula (XI) is added by the process described above in Step 2 to give a compound of the formula (IV).

In Step 4, a benzyl protecting group is removed from a compound of the formula (IV) by the process described in Step 1 to give a monosubstituted compound of the formula (V).

In Step 5, a compound of formula (V) is subjected to the urea anion formation described above in Step 2, afterwhich an benzylhalide of the formula (XII) is added by the process described above in Step 2 to give a compound of the formula (VI).

In Step 6, a compound of formula (V) is subjected to the urea anion formation described above in Step 2, afterwhich an alkylhalide of the formula (XI) is added by the process described above in Step 2 to give a compound of the formula (VII).

The present invention, by way of example and without limitation, may be further exemplified by reference to Scheme 2.

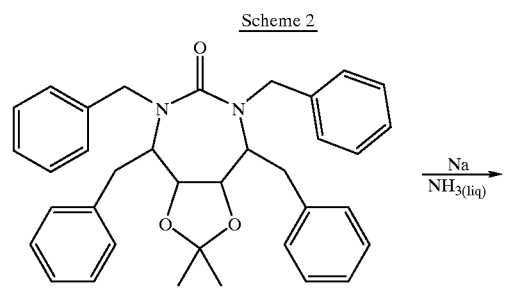

Scheme 2

23
-continued

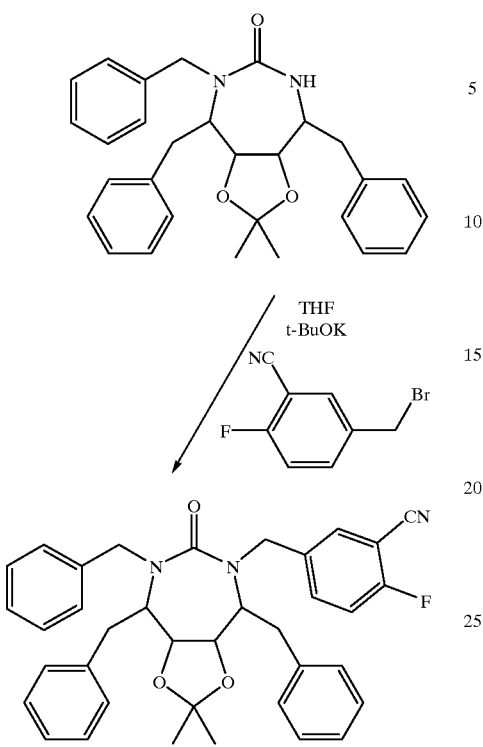

The following examples are meant to be illustrative of the present invention. These examples are presented to exemplify the invention and are not to be construed as limiting the inventor's scope.

Symmetrical dibenzylated cyclic ureas, as starting materials, and the alkylating agents of the invention can be prepared in a number of ways well known to one skilled in the art of organic synthesis. The starting materials and alkylating agents of the invention can be synthesized using the methods described in U.S. Pat. Nos. 5,532,356, 5,610,294, WO 93/07128, U.S. Pat. Nos. 5,530,124, 5,466,797, 5,559,252, and 5,637,780, the disclosures of which are hereby incorporated by reference. Additionally synthetic methods known in the art of organic synthesis can be combined with the above disclosed methods to enable all starting materials and alkylating agents.

As described herein, HPLC conditions for the determination of starting materials, products and intermediates are: Column: Zorbax Rx-C18 25 cm×3.9 mm; flow rate: 2.0 ml/minute; injection volume: 5 microliters; wavelength: 220 nm; Solvent A: 0.1% trifluoroacetic acid in water; Solvent B: 0.1% trifluoroacetic acid in acetonitrile; gradient timetable for solvents: T=0 minutes 50/50 A:B; T=20 minutes 5:95 A:B. As described herein, TLC conditions for the determination of starting materials, products and intermediates are 20% ethyl acetate 80% hexanes.

24
EXAMPLE 1

Monodebenzylation of a Symmetrical Cyclic Urea

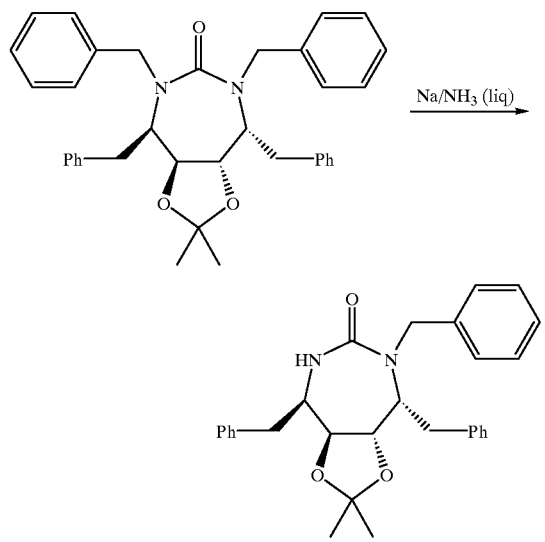

The starting material (2.29 g, 4.19 mmol) was dissolved in THF (3.5 ml) and the resulting solution added to a solution of sodium metal (0.29 g, 12.6 mmol) in liquid ammonia (20 ml) being stirred under argon. After one hour, the reaction was quenched by the addition of solid ammonium chloride (1.34 g, 25.1 mmol) and the ammonia allowed to evaporate under a nitrogen stream. The residue was partitioned between water and ethyl acetate. The organic phase was washed with brine, dried over sodium sulfate, filtered and evaporated to a white solid. The crude product was chromatographed on silica gel eluting with hexane/ethyl acetate (2/1) to give the desired product as a white foam (1.44 g, 75% yield). An analytical sample was recrystallized from ethyl acetate to give the product as a white solid, mp 155–156° C.

EXAMPLE 2

Monodebenzylation of a Symmetrical Cyclic Urea

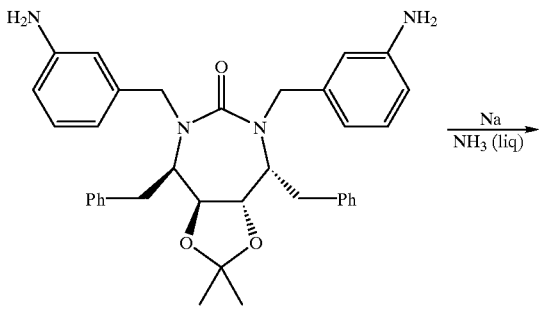

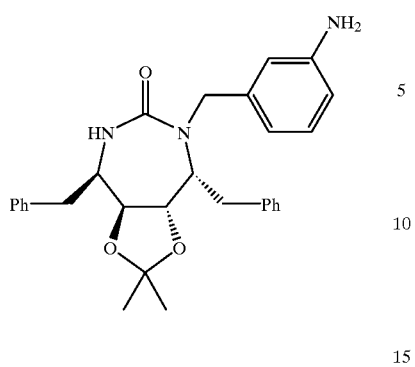

The starting material (25.0 g, 43.3 mmol) was dissolved in THF and added over one hour to a solution of sodium metal (3.45 g, 150 mmol) in liquid ammonia (100 ml) at −33° C. being stirred under argon. After another 30 minutes, HPLC analysis showed the absence of starting material. The reaction was quenched by the addition of ammonium chloride (10 g, 187 mmol) and the ammonia allowed to evaporate under an argon stream. The residue was partitioned between ethyl acetate (150 ml) and water (100 ml). The organic phase was washed with water (100 ml) and evaporated to an oil. The crude product was dissolved in 2-propanol (60 ml) and stirred at 80° C. while n-heptane (125 ml) was slowly added. Slow cooling to 21° C. over two hours resulted in a slurry which was cooled to 5° C., filtered and washed with n-heptane (3×50 ml). The solid was dried in a vacuum oven at 50° C. to provide the product (17.5 g, 86% yield), mp 164–165° C.

EXAMPLE 3

Monodebenzylation of a Symmetrical Cyclic Urea

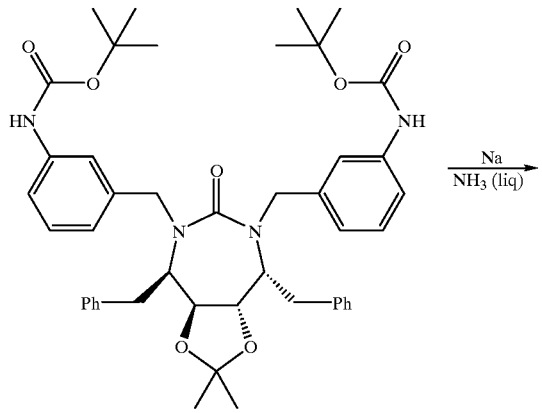

The starting material (144 g, 186 mmol) was dissolved in 750 ml of THF and added over about 20 minutes to a solution of sodium metal (14.96 g, 651 mmol) in liquid ammonia (750 ml) at −33° C. being stirred under argon. Additional sodium (5.5 g, 444 mmol) was added after HPLC showed starting material remained. After about one hour of stirring HPLC area % under the curve showed no starting material remained. The reaction was quenched by the addition of ammonium chloride (150 g) and the ammonia allowed to evaporate under a flow of nitrogen. THF (300 ml) and isopropyl alcohol (300 ml) were added to the flask, stirred for 2–3 hours, after which 200 ml of water were added and the solution stirred for an additional 30 minutes. The solid formed was filtered and taken up into thyl acetate with heating. The ethyl acetate solution was washed with water and the layers separated. After separation the organic solvent was removed and the solid taken up into 100 ml of hot isopropyl alcohol. The IPA solution was cooled slowly to 4° C. and then filtered. The filter cake was dried in an oven at about 60° C. overnight. Yield 70%.

EXAMPLE 4

Monodebenzylation of a Symmetrical Cyclic Urea

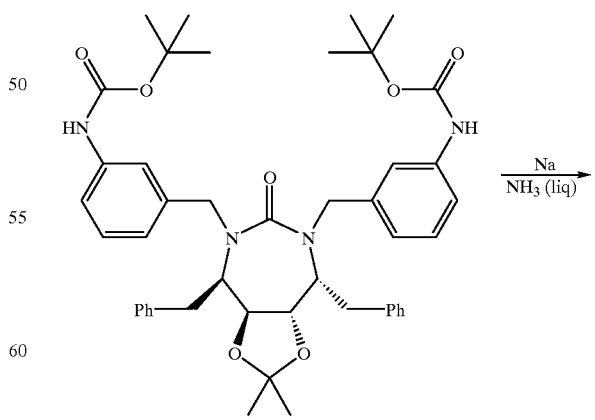

-continued

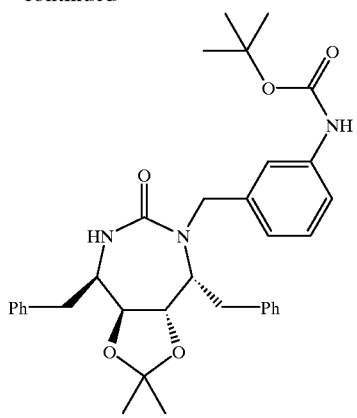

The starting material (228 g, 293 mmol) was dissolved in 1200 ml of THF and added over about 20 minutes to a solution of sodium metal (23.6 g, 1026 mmol) in 1200 ml of liquid ammonia at −33° C. being stirred under argon. Additional sodium (10.2 g, 444 mmol) was added after HPLC showed starting material remained, accounting for two extra acidic amide protons. After about one hour of stirring HPLC area % under the curve for starting material was about 8% and 92% for monodebenzylated product. The reaction was quenched by the addition of ammonium chloride (236 g) and the ammonia allowed to evaporate under a flow of nitrogen while stirring overnight. Dissolved the residue in 700 ml of water and 1.2 liters of ethyl acetate and separated the layers. The solvent is stripped off and the residue dissolved in about 50 ml isopropyl alcohol, followed by heating to 78° C. The solution is slowly cooled to room temperature followed by further cooling to 0° C. and filtered. The filter cake was rinsed with cold isopropyl alcohol and dried. Yield 76%.

EXAMPLE 5

Alkylation of a Monosubstituted Cyclic Urea to Give a Disubstituted Assymetric Cyclic Urea

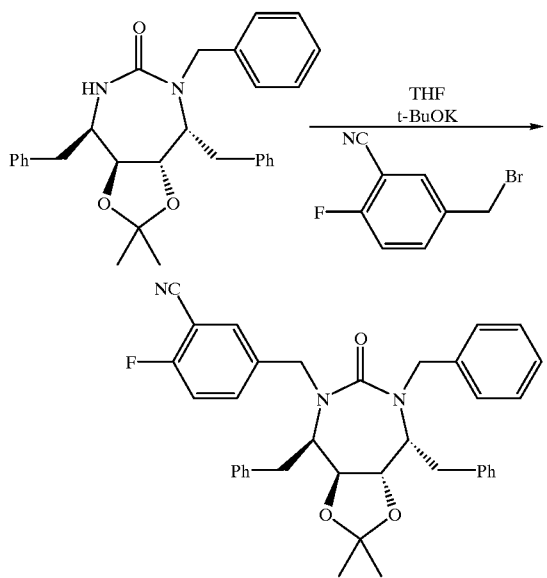

The starting material (14.7 g, 32.2 mmol) was dissolved in THF (140 ml) and stirred at 5° C. while a solution of potassium t-butoxide (38.6 ml, 1 M in THF, 38.6 mmol) was added. After another 20 minutes at 5° C., a solution of 5-bromomethyl-2-fluorobenzonitrile (8.53 g, 46.4 mmol) in THF (25 ml) was added. The reaction mixture was then stirred at ambient temperature for two hours, washed with brine (50 ml), dried over magnesium sulfate, filtered and evaporated to give the crude product. The residue was chromatographed on silica gel eluting with hexane/ethyl acetate (4/1) to afford the product as a white solid (16.2 g, 85% yield), mp 65–67° C.

EXAMPLE 6

Alkylation of a Monosubstituted Cyclic Urea to Give a Disubstituted Assymetric Cyclic Urea

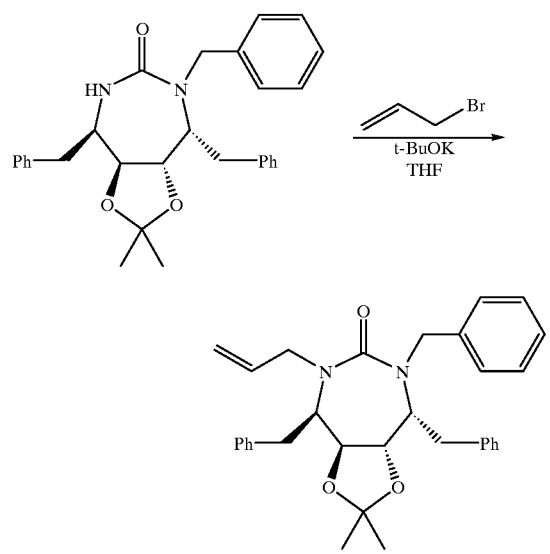

The starting material (3.22 g, 7.05 mmol) was dissolved in THF (100 ml) and stirred under nitrogen while a solution of potassium t-butoxide (10.6 ml, 1.0 M in THF, 10.6 mmol) was added followed by allyl bromide (1.22 ml, 14.1 mmol). The reaction was stirred at room temperature overnight. The resulting suspension was partitioned between ethyl acetate and water. The organic phase was washed with water and brine, dried over sodium sulfate, filtered and evaporated to an oil. The crude product was dissolved in hot 2-propanol (20 ml); water (20 ml) was added and the solution stirred at ambient temperature overnight. The resulting suspension was cooled to 5° C., filtered and washed with cold 2-propanol/water (10 ml, 1/1). The solid was dried in a vacuum oven at 40° C. to give the final product (2.38 g, 68% yield), mp 104–105° C.

EXAMPLE 7

Alkylation of a Monosubstituted Cyclic Urea to Give a Disubstituted Assymetric Cyclic Urea

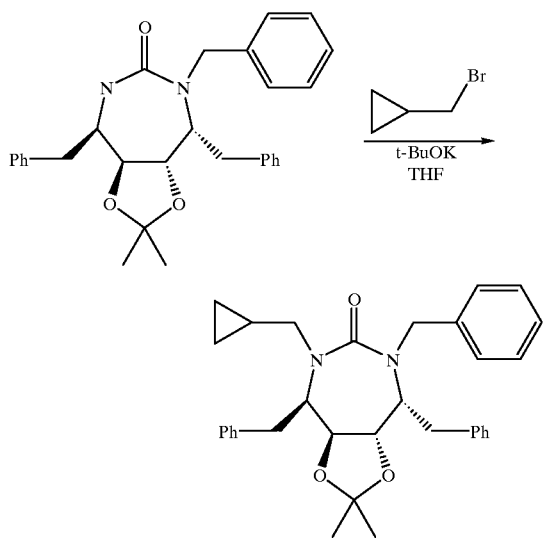

The starting material (0.40 g, 0.88 mmol) was dissolved in THF (20 ml) and stirred under nitrogen while a solution of potassium t-butoxide (1.31 ml, 1.0 M in THF, 1.31 mmol) was added followed by cyclopropylmethyl bromide (0.127 ml, 1.31 mmol). The mixture was heated at reflux overnight. The resulting suspension was partitioned between ethyl acetate and water. The organic phase was washed with water and brine, dried over sodium sulfate, filtered and evaporated to a wax. The crude product was chromatographed on silica gel eluting with methylene chloride to provide the final product as a white foam (0.35 g, 78% yield); mass spectrum (CI/NH$_3$): m/e=511 (M+H$^+$).

EXAMPLE 8

Debenzylation of an Assymmetrical Cyclic Urea

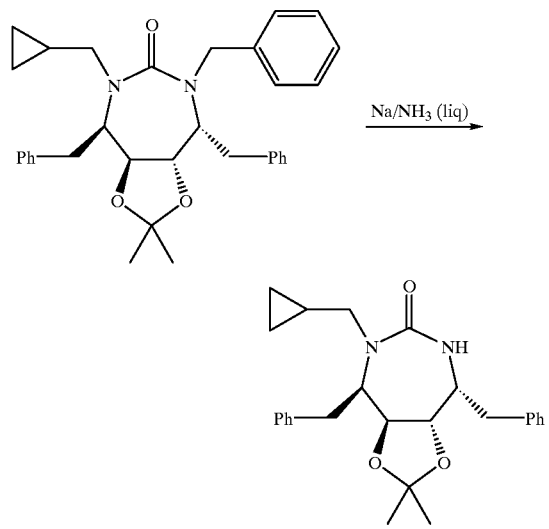

The starting material (0.77 g, 1.51 mmol) was dissolved in THF (3.0 ml) and added to a solution of sodium metal (0.10 g, 4.53 mmol) in liquid ammonia (15 ml) being stirred under argon. After one hour, the reaction was quenched by the addition of solid ammonium chloride (0.48 g, 9.06 mmol) and the ammonia allowed to evaporate under a nitrogen stream. The residue was partitioned between water and ethyl acetate. The organic phase was washed with brine, dried over sodium sulfate, filtered and evaporated to give final product as a pale yellow foam (0.61 g, 97% yield); mass spectrum (CI/NH$_3$): m/e=421 (M+H$^+$).

What is claimed is:

1. A process for the preparation of a compound of formula (II):

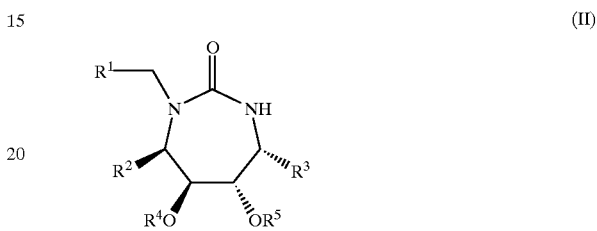

wherein:

R$^1$ is phenyl substituted with 0–3 R$^{1a}$;

R$^{1a}$ is selected from one or more of the following:
C$_1$–C$_8$ alkyl, C$_3$–C$_{10}$ cycloalkyl, C$_2$–C$_6$ alkoxyalkyl, C$_1$–C$_4$ haloalkyl, C$_1$–C$_4$ haloalkoxy, phenyl, napthyl, halogen, —NHSO$_2$R$^{17a}$, —NR$^{16}$R$^{17}$, —OR$^{17}$, —C(=O)NR$^{16}$R$^{17}$, —NR$^{16}$C(=O)R$^{17a}$, —OC(=O)NR$^{16}$R$^{17}$, —C(=O)R$^{17a}$, —NR$^{16}$CO$_2$R$^{17a}$, —SONR$^{16}$R$^{17}$, and —SO$_2$NR$^{16}$R$^{17}$;

R$^{16}$ is independently hydrogen or C$_1$–C$_4$ alkyl;

R$^{17}$ is independently selected from:
hydrogen, C$_1$–C$_4$ alkyl, an amine protecting group when R$^{17}$ is bonded to N, and a hydroxyl protecting group when R$^{17}$ is bonded to O;

R$^{17a}$ is C$_1$–C$_4$ alkyl;

R$^2$ and R$^3$ are the same and individually selected from:
benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl; and R$^4$ and R$^5$ are the same and individually a hydroxyl protecting group;

alternatively, R$^4$ and R$^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_2$CH$_2$CH$_2$CH$_3$)$_2$—O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

the process, comprising:

(1) contacting, at a suitable temperature for a sufficient amount of time, a solution of about 2.7 to about 4.4 equivalents of alkali metal dissolved in ammonia with about one equivalent of a compound of formula (I):

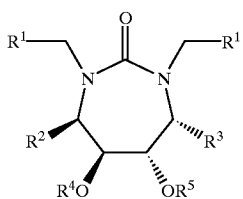
(I)

in an aprotic solvent;

(2) quenching the reaction of step (1) by addition of a suitable quenching agent to form a compound of formula (II); and (3) isolating the product.

2. A process according to claim 1 for the preparation of a compound of formula (II), wherein:

$R^1$ is phenyl substituted with 0–2 $R^{1a}$;

$R^{1a}$ is selected from one or more of the following:
$C_1$–$C_4$ alkyl, phenyl, $C_1$–$C_2$ haloalkyl, halogen, —NHSO$_2$R$^{17a}$, —NR$^{16}$R$^{17}$, —OR$^{17}$, —C (=O) NR$^{16}$R$^{17}$, —NR$^{16}$C(=O)R$^{17a}$, —OC(=O)NR$^{16}$R$^{17}$, —C(=O)R$^{17a}$, —NR$^{16}$CO$_2$R$^{17a}$, and —SO$_2$NR$^{16}$R$^{17}$;

$R^2$ and $R^3$ are the same and individually selected from: benzyl, fluorobenzyl, methoxybenzyl, methylbenzyl, isobutyl, aminobenzyl, and hydroxybenzyl; and $R^4$ and $R^5$ are the same and individually a hydroxyl protecting group;

alternatively, $R^4$ and $R^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—CH(phenyl)—O—, —OCH$_2$SCH$_2$O—, —OCH$_2$OCH$_2$O—, —OC(CH$_3$)$_2$O, and —OC(=O)O—.

3. A process according to claim 2 for the preparation of a compound of formula (II):

the process, comprising:

(1) contacting, at about –78° C. to about –33° C. for about 5 minutes to about 60 minutes, a solution of about 2.7 to about 4.4 equivalents of sodium metal dissolved in ammonia with about one equivalent of a compound of formula (I) in an aprotic solvent, selected from the group: tetrahydrofuran, diethyl ether, ethylene glycol, dimethyl ether, t-butyl methyl ether, hexane, heptane, and cyclohexane;

(2) quenching the reaction of step (1) by addition of a suitable quenching agent, selected from the group: ammonium chloride, ammonium bromide and ammonium iodide;

to form a compound of formula (II); and (3) isolating the product.

4. A process according to claim 3 for the preparation of a compound of formula (II-i):

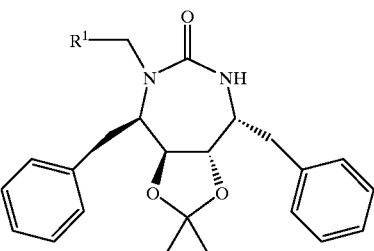
(II-i)

wherein:
$R^1$ is phenyl substituted with 0–2 $R^{1a}$;
$R^{1a}$ is selected from one or more of the following:
$C_1$–$C_4$ alkyl, halogen, and —NR$^{16}$R$^{17}$;
$R^{16}$ is independently hydrogen or $C_1$–$C_4$ alkyl;
$R^{17}$ is independently selected from hydrogen, $C_1$–$C_4$ alkyl, and an amine protecting group;

said process comprising:

(1) contacting, at about –33° C. for about 15 minutes to about 60 minutes, a solution of about 2.9 to about 3.5 equivalents of sodium metal dissolved in ammonia with about one equivalent of a compound of formula (I-i):

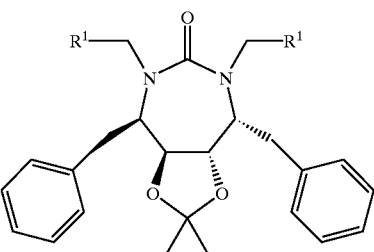
(I-i)

in an aprotic solvent solvent;

(2) quenching the reaction of step (1) by addition of ammonium chloride to form a compound of formula (II-i); and (3) isolating the product.

5. A process according to claim 4 for the preparation of a compound of formula (II-i) wherein the aprotic solvent is tetrahydrofuran.

6. A process for the preparation of a compound of formula (III):

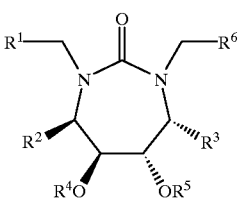
(III)

wherein:
$R^1$ is phenyl substituted with 0–3 $R^{1a}$;
$R^{1a}$ is selected from one or more of the following:
$C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, $-NHSO_2R^{17a}$, $-NR^{16}R^{17}$, $-OR^{17}$, $-C(=O)NR^{16}R^{17}$, $-NR^{16}C(=O)R^{17a}$, $-OC(=O)NR^{16}R^{17}$, $-C(=O)R^{17a}$, $-NR^{16}CO_2R^{17a}$, $-SONR^{16}R^{17}$, and $-SO_2NR^{16}R^{17}$;

$R^{16}$ is independently hydrogen or $C_1-C_4$ alkyl;

$R^{17}$ is independently selected from:
 hydrogen, $C_1-C_4$ alkyl, an amine protecting group when $R^{17}$ is bonded to N, and a hydroxyl protecting group when $R^{17}$ is bonded to O;

$R^{17a}$ is $C_1-C_4$ alkyl;

$R^2$ and $R^3$ are the same and individually selected from:
 benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;

$R^4$ and $R^5$ are the same and individually a hydroxyl protecting group;

alternatively, $R^4$ and $R^5$ may be taken together along with the oxygen atoms to which they are attached to form a group selected from the group consisting of:
 $-O-C(-CH_2CH_2CH_2CH_2-)-O-$, $-O-C(CH_2CH_3)_2O-$, $-O-C(CH_3)(CH_2CH_3)-O-$, $-O-C(CH_2CH_2CH_2CH_3)_2O-$, $-O-C(CH_3)(CH_2CH(CH_3)CH_3)-O-$, $-O-CH(phenyl)-O-$, $-OCH_2SCH_2O-$, $-OCH_2OCH_2O-$, $-OC(=O)O-$, $-OCH_2O-$, $-OC(=S)O-$, $-OC(=O)C(=O)O-$, $-OC(CH_3)_2O-$, and $-OC(OCH_3)(CH_2CH_2CH_3)O-$;

$R^6$ is phenyl substituted with 0–3 $R^{6a}$;

$R^{6a}$ is selected from one or more of the following:
 $C_1-C_8$ alkyl, $C_2-C_4$ alkenyl, $C_2-C_4$ alkynyl, $C_3-C_{10}$ cycloalkyl, $C_2-C_6$ alkoxyalkyl, $C_1-C_4$ haloalkyl, $-NHSO_2R^{19a}$, phenyl, $-OH$, halogen, azido, $-CO_2R^{19}$, cyano, $-NR^{18}R^{19}$, $-OR^{19}$, $-NO_2$, $-SO_2NR^{18}R^{19}$, $-C(=O)NR^{18}R^{19}$, $-NR^{18}C(=O)R^{19}$, $-OC(=O)NR^{18}R^{19}$, $-C(=O)R^{19}$, $-OC(=O)R^{19}$, $-OCO_2R^{19}$, and $-NR^{18}CO_2R^{19}$;

$R^{18}$ is independently selected from hydrogen and $C_1-C_4$ alkyl;

$R^{19}$ is independently selected from:
 hydrogen, $C_1-C_4$ alkyl, phenyl, haloalkyl, an amine protecting group when $R^{19}$ is bonded to N, and a hydroxyl or carboxyl protecting group when $R^{19}$ is bonded to O; and $R^{19a}$ is $C_1-C_4$ alkyl;

said process comprising:

(1) contacting, at a suitable temperature for a sufficient amount of time, a solution of about 2.7 to about 4.4 equivalents of alkali metal dissolved in ammonia with about one equivalent of a compound of formula (I):

(I)

in an aprotic solvent;

(2) quenching the reaction of step (1) by addition of a suitable quenching agent to form a compound of formula (II):

(II)

(3) isolating a compound of formula (II); and (4) contacting a compound of formula (II) with at least one equivalent of a strong base and at least one equivalent a compound of formula (X):

$$Z^1-CH_2-R^6 \qquad (X)$$

wherein:
 $Z^1$ is chlorine, bromine, or iodine;

in a second aprotic solvent for a sufficient amount of time to effect formation of a compound of formula (III).

7. A process according to claim 6 for the preparation of a compound of formula (III), wherein;

$R^1$ is phenyl substituted with 0–2 $R^{1a}$;

$R^{1a}$ is selected from one or more of the following:
 $C_1-C_4$ alkyl, phenyl, $C_1-C_2$ haloalkyl, halogen, $-NHSO_2R^{17a}$, $-NR^{16}R^{17}$, $-OR^{17}$, $-SO_2NR^{16}R^{17}$, $-C(=O)NR^{16}R^{17}$, $-NR^{16}C(=O)R^{17a}$, $-OC(=O)NR^{16}R^{17}$, $-C(=O)R^{17a}$, and $-NR^{16}CO_2R^{17a}$;

$R^2$ and $R^3$ are the same and individually selected from:
 benzyl, fluorobenzyl, methoxybenzyl, methylbenzyl, isobutyl, aminobenzyl, and hydroxybenzyl;

$R^4$ and $R^5$ are the same and individually a hydroxyl protecting group;

alternatively, $R^4$ and $R^5$ may be taken together along with the oxygen atoms to which they are attached to form a group selected from the group consisting of:
 $-O-C(-CH_2CH_2CH_2CH_2CH_2-)-O-$, $-O-C(CH_2CH_3)_2O-$, $-O-CH(phenyl)-O-$, $-OCH_2SCH_2O-$, $-OCH_2OCH_2O-$, $-OC(CH_3)_2O$, and $-OC(=O)O-$;

$R^6$ is phenyl substituted with 0–2 $R^{6a}$;

$R^{6a}$ is selected from one or more of the following:
 $C_1-C_3$ alkyl, $C_1-C_2$ haloalkyl, $-NHSO_2R^{19}$, $-OH$, halogen, azido, $-CO_2R^{19}$, cyano, $-NR^{18}R^{19}$, $-OR^{19}$, $-NO_2$, $-SO_2NR^{18}R^{19}$, $-C(=O)NR^{18}R^{19}$, $-NR^{18}C(=O)R^{19}$, $-OC(=O)NR^{18}R^{19}$, $-C(=O)R^{19}$, and $-OC(=O)R^{19}$;

$R^{18}$ is independently selected from hydrogen and $C_1-C_4$ alkyl; and $R^{19}$ is independently selected from:
 hydrogen, $C_1-C_4$ alkyl, phenyl, an amine protecting group when $R^{19}$ is bonded to N, and a hydroxyl or carboxyl protecting group when $R^{19}$ is bonded to O.

8. A process according to claim 7 for the preparation of a compound of formula (III);

the process, comprising:

(1) contacting, at about $-78°$ C. to about $-33°$ C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:

tetrahydrofuran, diethyl ether, ethylene glycol, dimethyl ether, t-butyl methyl ether, hexane, heptane, and cyclohexane;
(2) quenching the reaction of step (1) by addition of a suitable quenching agent, selected from the group: ammonium chloride, ammonium bromide and ammonium iodide;
to form a compound of formula (II);
(3) isolating a compound of formula (II); and
(4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;
and at least one equivalent a compound of formula (X) in a second aprotic solvent selected from the group:
tetrahydrofuran, diethyl ether, ethylene glycol, dimethyl ether, t-butyl methyl ether, toluene, benzene, xylene, hexane, heptane, and cyclohexane;
for a about 10 minutes to about 24 hours to effect formation of a compound of formula (III).

9. A process according to claim 8 for the preparation of a compound of formula (III-i):

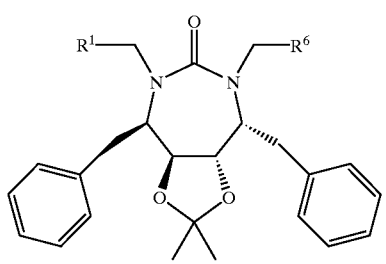

(III-i)

wherein:
$R^1$ is phenyl substituted with 0–2 $R^{1a}$;
$R^{1a}$ is selected from one or more of the following:
  $C_1$–$C_4$ alkyl, halogen, and —$NR^{16}R^{17}$;
$R^{16}$ is independently selected from hydrogen, $C_1$–$C_4$ alkyl, and an amine protecting group;
$R^{17}$ is independently selected from hydrogen, $C_1$–$C_4$ alkyl, and an amine protecting group;
$R^6$ is phenyl substituted with 0–2 $R^{6a}$;
$R^{6a}$ is selected from one or more of the following:
  $C_1$–$C_4$ alkyl, phenyl, —OH, halogen, —$CO_2R^{19}$, cyano, —$NR^{18}R^{19}$, —$OR^{19}$, —$NO_2$, —C(=O)$NR^{18}R^{19}$, —$NR^{18}$C(=O)$R^{19}$, —OC(=O)$NR^{18}R^{19}$, —C(=O)$R^{19}$, and —OC(=O)$R^{19}$;
$R^{18}$ is independently selected from hydrogen and $C_1$–$C_4$ alkyl; and
$R^{19}$ is independently selected from:
  hydrogen, $C_1$–$C_4$ alkyl, phenyl, an amine protecting group when $R^{19}$ is bonded to N, a hydroxyl or carboxyl protecting group when $R^{19}$ is bonded to O; and
said process comprising:
(1) contacting, at about −33° C. for about 15 minutes to about 60 minutes, a solution of about 2.9 to about 3.5 equivalents of sodium metal dissolved in ammonia with about one equivalent of a compound of formula (I-i):

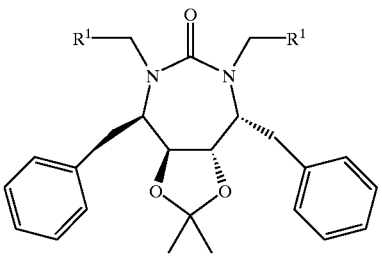

(I-i)

in an aprotic solvent;
(2) quenching the reaction of step (1) by addition of ammonium chloride to form a compound of formula (II-i);

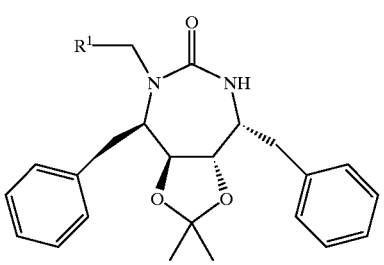

(II-i)

(3) isolating a compound of formula (II-i); and
(4) contacting a compound of formula (II-i) with at least one equivalent of potassium t-butoxide or sodium hydride and at least one equivalent a compound of formula (X):

$Z^1$—$CH_2$—$R^6$ (X)

wherein $Z^1$ is chlorine or bromine;
in a second aprotic for about 15 minutes to about 24 hours to effect formation of a compound of formula (III-i).

10. A process according to claim 9 for the preparation of a compound of formula (III-i), wherein the aprotic solvent is tetrahydrofuran and the second aprotic solvent is tetrahydrofuran.

11. A process for the preparation of a compound of formula (IV):

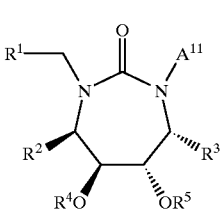

(IV)

wherein:
$R^1$ is phenyl substituted with 0–3 $R^{1a}$;
$R^{1a}$ is selected from one or more of the following:
  $C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —$NHSO_2R^{17a}$, —$NR^{16}R^{17}$, —$OR^{17}$, —C(=O)$NR^{16}R^{17}$, —$NR^{16}$C(=O)$R^{17a}$, —OC(=O)NR$^{16}$R$^{17}$, —C(=O)R$^{17a}$, —NR$^{16}$CO$_2$R$^{17a}$, —SONR$^{16}$R$^{17}$, and —SO$_2$NR$^{16}$R$^{17}$;

R$^{16}$ is independently hydrogen or C$_1$–C$_4$ alkyl;
R$^{17}$ is independently selected from:
hydrogen, C$_1$–C$_4$ alkyl, an amine protecting group when R$^{17}$ is bonded to N, and a hydroxyl protecting group when R$^{17}$ is bonded to O;
R$^{17a}$ is C$_1$–C$_4$ alkyl;
R$^2$ and R$^3$ are the same and individually selected from:
benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;
R$^4$ and R$^5$ are the same and individually a hydroxyl protecting group;
alternatively, R$^4$ and R$^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_3$CH$_2$CH$_2$CH$_3$)$_2$—O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

A$^{11}$ is C$_1$–C$_8$ alkyl substituted with 0–3 R$^{11}$;
R$^{11}$ is independently selected from the following:
C$_1$–C$_8$ alkyl, C$_2$–C$_4$ alkenyl, C$_2$–C$_4$ alkynyl, C$_3$–C$_{10}$ cycloalkyl, C$_2$–C$_6$ alkoxyalkyl, C$_1$–C$_4$ haloalkyl, —NHSO$_2$R$^{19a}$, phenyl, —OH, halogen, —NR$^{18}$R$^{19}$, —OR$^{19}$, —NO$_2$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19a}$, and —NR$^{18}$CO$_2$R$^{19}$;
R$^{18}$ is independently selected from hydrogen and C$_1$–C$_4$ alkyl;
R$^{19}$ is independently selected from:
hydrogen, C$_1$–C$_4$ alkyl, phenyl, haloalkyl, an amine protecting group when R$^{19}$ is bonded to N, and a hydroxyl or carboxyl protecting group when R$^{19}$ is bonded to O; and
R$^{19a}$ is C$_1$–C$_4$ alkyl;
said process comprising:
(1) contacting, at a suitable temperature for a sufficient amount of time, a solution of about 2.7 to about 4.4 equivalents of alkali metal dissolved in ammonia with about one equivalent of a compound of formula (I):

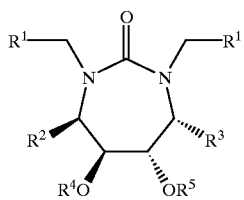

(I)

in an aprotic solvent;
(2) quenching the reaction of step (1) by addition of a suitable quenching agent to form a compound of formula (II);

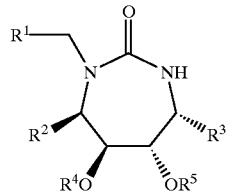

(II)

(3) isolating a compound of formula (II); and
(4) contacting a compound of formula (II) with at least one equivalent of a strong base and at least one equivalent a compound of formula (XI):

Z$^2$—A$^{11}$ (XI)

wherein Z$^2$ is chlorine, bromine, or iodine;
in a second aprotic solvent for a sufficient amount of time to effect formation of a compound of formula (IV).

12. A process according to claim 11 for the preparation of a compound of formula (IV), wherein;
R$^1$ is phenyl substituted with 0–2 R$^{1a}$;
R$^{1a}$ is selected from one or more of the following:
C$_1$–C$_4$ alkyl, phenyl, C$_1$–C$_2$ haloalkyl, halogen, —NHSO$_2$R$^{17a}$, —NR$^{16}$R$^{17}$, —OR$^{17}$, —SO$_2$NR$^{16}$R$^{17}$, —C(=O)NR$^{16}$R$^{17}$, —NR$^{16}$C(=O)R$^{17a}$, —OC(=O)NR$^{16}$R$^{17}$, —C(=O)R$^{17a}$, and —NR$^{16}$CO$_2$R$^{17a}$;
R$^2$ and R$^3$ are the same and individually selected from:
benzyl, fluorobenzyl, methoxybenzyl, methylbenzyl, isobutyl, aminobenzyl, and hydroxybenzyl;
R$^4$ and R$^5$ are the same and individually a hydroxyl protecting group;
alternatively, R$^4$ and R$^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—CH(phenyl)—O—, —OCH$_2$SCH$_2$O—, —OCH$_2$OCH$_2$O—, —OC(CH$_3$)$_2$O, and —OC(=O)O—;
A$^{11}$ is C$_1$–C$_4$ alkyl substituted with 0–3 R$^{11}$;
R$^{11}$ is independently selected from the following:
C$_1$–C$_4$ alkyl, C$_2$–C$_4$ alkenyl, C$_3$–C$_6$ cycloalkyl, C$_1$–C$_4$ haloalkyl, —NHSO$_2$R$^{19a}$, phenyl, halogen, —NR$^{18}$R$^{19}$, —OR$^{19}$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19a}$, and —NR$^{18}$CO$_2$R$^{19}$,
R$^{18}$ is independently selected from hydrogen and C$_1$–C$_4$ alkyl;
R$^{19}$ is independently selected from:
hydrogen, C$_1$–C$_4$ alkyl, phenyl, haloalkyl, an amine protecting group when R$^{19}$ is bonded to N, and a hydroxyl or carboxyl protecting group when R$^{19}$ is bonded to O; and
R$^{19a}$ is C$_1$–C$_4$ alkyl.

13. A process according to claim 12 for the preparation of a compound of formula (IV):
the process, comprising:
(1) contacting, at about −78° C. to about −33° C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:
tetrahydrofuran, diethyl ether, ethylene glycol, dimethyl ether, t-butyl methyl ether, hexane, heptane, and cyclohexane;
(2) quenching the reaction of step (1) by addition of a suitable quenching agent, selected from the group: ammonium chloride, ammonium bromide and ammonium iodide;
to form a compound of formula (II);
(3) isolating a compound of formula (II); and
(4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;
and at least one equivalent a compound of formula (XI) in a second aprotic solvent selected from the group:
tetrahydrofuran, diethyl ether, ethylene glycol, dimethyl ether, t-butyl methyl ether, toluene, benzene, xylene, hexane, heptane, and cyclohexane;
for a about 10 minutes to about 24 hours to effect formation of a compound of formula (IV).

14. A process according to claim 13 for the preparation of a compound of formula (IV-i):

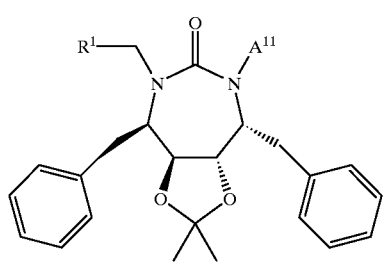

(IV-i)

wherein:
$R^1$ is phenyl substituted with 0–2 $R^{1a}$;
$R^{1a}$ is selected from one or more of the following:
$C_1$–$C_4$ alkyl, halogen, and —$NR^{16}R^{17}$;
$R^{16}$ is independently hydrogen or $C_1$–$C_4$ alkyl;
$R^{17}$ is independently selected from hydrogen, $C_1$–$C_4$ alkyl, and an amine protecting group;
$A^{11}$ is $C_1$–$C_4$ alkyl substituted with 0–3 $R^{11}$;
$R^{11}$ is independently selected from the following:
$C_1$–$C_4$ alkyl, $C_2$–$C_4$ alkenyl, $C_3$–$C_6$ cycloalkyl, $C_1$–$C_4$ haloalkyl, —$NHSO_2R^{19a}$, phenyl, halogen, —$NR^{18}R^{19}$, —$OR^{19}$, —$SO_2NR^{18}R^{19}$, —$C(=O)NR^{18}R^{19}$, —$NR^{18}C(=O)R^{19}$, —$OC(=O)NR^{18}R^{19}$, —$C(=O)R^{19a}$, and —$NR^{18}CO_2R^{19}$,
$R^{18}$ is independently selected from hydrogen and $C_1$–$C_4$ alkyl; and
$R^{19}$ is independently selected from:
hydrogen, $C_1$–$C_4$ alkyl, phenyl, an amine protecting group when $R^{19}$ is bonded to N, a hydroxyl or carboxyl protecting group when $R^{19}$ is bonded to O;
said process comprising:
(1) contacting, at about –33° C. for about 15 minutes to about 60 minutes, a solution of about 2.9 to about 3.5 equivalents of sodium metal dissolved in ammonia with about one equivalent of a compound of formula (I-i):

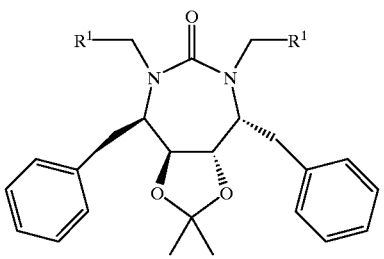

(I-i)

in an aprotic solvent;
(2) quenching the reaction of step (1) by addition of ammonium chloride to form a compound of formula (II-i);

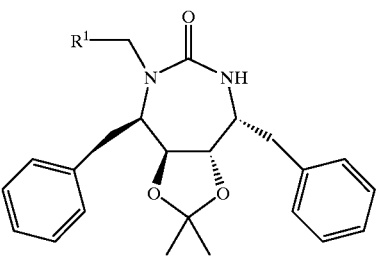

(II-i)

(3) isolating a compound of formula (II-i); and
(4) contacting a compound of formula (II-i) with at least one equivalent of potassium t-butoxide or sodium hydride and at least one equivalent a compound of formula (XI):

$$Z^2—A^{11} \qquad (XI)$$

wherein $Z^2$ is chlorine or bromine;
in a second aprotic for about 15 minutes to about 24 hours to effect formation of a compound of formula (IV-i).

15. A process according to claim 14 for the preparation of a compound of formula (IV-i), wherein the aprotic solvent is tetrahydrofuran and the second aprotic solvent is tetrahydrofuran.

16. A process for the preparation of a compound of formula (VI):

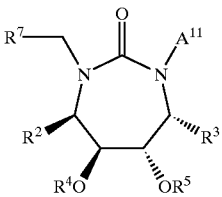

(VI)

wherein:
$R^2$ and $R^3$ are the same and individually selected from:
benzyl, fluorobenzyl, methoxybenzyl, methylbenzyl, isobutyl, aminobenzyl, hydroxybenzyl, pyridylmethyl, naphthylmethyl, thiomethylbenzyl, 3,4-methylene-dioxybenzyl, and N,N-dimethylaminobenzyl;

$R^4$ and $R^5$ are the same and individually a hydroxyl protecting group;

alternatively, $R^4$ and $R^5$ may be taken together along with the oxygen atoms to which they are attached to form a group selected from the group consisting of:
—O—C(—CH$_2$CH$_2$CH$_2$CH$_2$CH$_2$—)—O—, —O—C(CH$_2$CH$_3$)$_2$O—, —O—C(CH$_3$)(CH$_2$CH$_3$)—O—, —O—C(CH$_2$CH$_2$CH$_2$CH$_3$)$_2$O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OC(=O)O—, —OCH$_2$O—, —OC(=S)O—, —OC(=O)C(=O)O—, —OC(CH$_3$)$_2$O—, and —OC(OCH$_3$)(CH$_2$CH$_2$CH$_3$)O—;

$R^7$ is phenyl substituted with 0–3 $R^{7a}$;

$R^{7a}$ is selected from one or more of the following:
$C_1$–$C_8$ alkyl, $C_2$–$C_4$ alkenyl, $C_2$–$C_4$ alkynyl, $C_3$–$C_{10}$ cycloalkyl, $C_2$–$C_6$ alkoxyalkyl, $C_1$–$C_4$ haloalkyl, —NHSO$_2$R$^{19a}$, phenyl, —OH, halogen, azido, —CO$_2$R$^{19}$, cyano, —NR$^{18}$R$^{19}$, —OR$^{19}$, —NO$_2$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19}$, —OC(=O)R$^{19}$, —OCO$_2$R$^{19}$, and —NR$^{18}$CO$_2$R$^{19}$;

$A^{11}$ is $C_1$–$C_8$ alkyl substituted with 0–3 $R^{11}$;

$R^{11}$ is independently selected from the following:
$C_1$–$C_8$ alkyl, $C_2$–$C_4$ alkenyl, $C_2$–$C_4$ alkynyl, $C_3$–$C_{10}$ cycloalkyl, $C_2$–$C_6$ alkoxyalkyl, $C_1$–$C_4$ haloalkyl, —NHSO$_2$R$^{19a}$, phenyl, —OH, halogen, —NR$^{18}$R$^{19}$, —OR$^{19}$, —SO$_2$NR$^{18}$R$^{19}$, —C(=O)NR$^{18}$R$^{19}$, —NR$^{18}$C(=O)R$^{19}$, —OC(=O)NR$^{18}$R$^{19}$, —C(=O)R$^{19a}$, and —NR$^{18}$CO$_2$R$^{19}$;

$R^{18}$ is independently selected from hydrogen and $C_1$–$C_4$ alkyl;

$R^{19}$ is independently selected from:
hydrogen, $C_1$–$C_4$ alkyl, phenyl, haloalkyl, an amine protecting group when $R^{19}$ is bonded to N, and a hydroxyl or carboxyl protecting group when $R^{19}$ is bonded to O; and $R^{19a}$ is $C_1$–$C_4$ alkyl;

said process comprising:

(1) contacting, at a suitable temperature for a sufficient amount of time, a solution of about 2.7 to about 4.4 equivalents of alkali metal dissolved in ammonia with about one equivalent of a compound of formula (I):

(I)

<chemical structure> wherein:

$R^1$ is phenyl substituted with 0–3 $R^{1a}$;

$R^{1a}$ is selected from one or more of the following:
$C_1$–$C_8$ alkyl, $C_3$–$C_{10}$ cycloalkyl, $C_2$–$C_6$ alkoxyalkyl, $C_1$–$C_4$ haloalkyl, $C_1$–$C_4$ haloalkoxy, phenyl, napthyl, halogen, —NHSO$_2$R$^{17a}$, —NR$^{16}$R$^{17}$, —OR$^{17}$, —C(=O)NR$^{16}$R$^{17}$, —NR$^{16}$C(=O)R$^{17a}$, —OC(=O)NR$^{16}$R$^{17}$, C(=O)R$^{17a}$, —NR$^{16}$CO$_2$R$^{17a}$, —SONR$^{16}$R$^{17}$, and —SO$_2$NR$^{16}$R$^{17}$;

$R^{16}$ is independently hydrogen or $C_1$–$C_4$ alkyl;

$R^{17}$ is independently selected from:
hydrogen, $C_1$–$C_4$ alkyl, an amine protecting group when $R^{17}$ is bonded to N, and a hydroxyl protecting group when $R^{17}$ is bonded to O;

$R^{17a}$ is $C_1$–$C_4$ alkyl;

in an aprotic solvent;

(2) quenching the reaction of step (1) by addition of a suitable quenching agent to form a compound of formula (II);

(II)

<chemical structure>

(3) isolating a compound of formula (II); and (4) contacting a compound of formula (II) with at least one equivalent of a strong base and at least one equivalent a compound of formula (XI):

$$Z^2-A^{11} \qquad (XI)$$

wherein $Z^2$ is chlorine, bromine, or iodine;

in a second aprotic solvent for a sufficient amount of time to effect formation of a compound of formula (IV);

(IV)

<chemical structure>

(5) contacting, at a suitable temperature for a sufficient amout of time, a solution of about 2.7 to about 4.4 equivalents of alkali metal dissolved in ammonia with about one equivalent of a compound of formula (IV) in a third aprotic solvent;

(6) quenching the reaction of step (5) by addition of a suitable second quenching agent to form a compound of formula (V); and (V)

<chemical structure>

(7) isolating a compound of formula (V); and (8) contacting a compound of formula (V) with at least one equivalent of a second strong base and at least one equivalent a compound of formula (XII), $$Z^3-CH_2-R^7 \qquad (XII)$$

wherein $Z^3$ is chlorine, bromine or iodine;
in fourth aprotic solvent for a sufficient amount of time to effect formation of a compound of formula (VI).

17. A process according to claim 16 for the preparation of a compound of formula (IV), wherein;
$R^1$ is phenyl substituted with 0–2 $R^{1a}$;
$R^{1a}$ is selected from one or more of the following:
$C_1$–$C_4$ alkyl, phenyl, $C_1$–$C_2$ haloalkyl, halogen, —$NHSO_2R^{17a}$, —$NR^{16}R^{17}$, —$OR^{17}$, —$SO_2NR^{16}R^{17}$, —$C(=O)NR^{16}R^{17}$, —$NR^{16}C(=O)R^{17a}$, —$OC(=O)NR^{16}R^{17}$, —$C(=O)R^{17a}$, and —$NR^{16}CO_2R^{17a}$;
$R^2$ and $R^3$ are the same and individually selected from: benzyl, fluorobenzyl, methoxybenzyl, methylbenzyl, isobutyl, aminobenzyl, and hydroxybenzyl;
$R^4$ and $R^5$ are the same and individually a hydroxyl protecting group;
alternatively, $R^4$ and $R^5$ may be taken together along with the oxygen atoms to which they are attached to form a group selected from the group consisting of:
—O—C(—$CH_2CH_2CH_2CH_2CH_2$—)—O—, —O—C($CH_2CH_3$)$_2$O—, —O—CH(phenyl)—O—, —$OCH_2SCH_2$O—, —$OCH_2OCH_2$O—, —OC($CH_3$)$_2$O, and —OC(=O)O—;
$R^7$ is phenyl substituted with 0–3 $R^{7a}$
$R^{7a}$ is selected from one or more of the following:
$C_1$–$C_3$ alkyl, $C_1$–$C_2$ haloalkyl, —$NHSO_2R^{19a}$, —OH, halogen, azido, —$CO_2R^{19}$, cyano, —$NR^{18}R^{19}$, —$OR^{19}$, —$NO_2$, —$SO_2NR^{18}R^{19}$, —$C(=O)NR^{18}R^{19}$, —$NR^{18}C(=O)R^{19}$, —$OC(=O)NR^{18}R^{19}$, —$C(=O)R^{19}$, and —$OC(=O)R^{19}$;
$A^{11}$ is $C_1$–$C_4$ alkyl substituted with 0–3 $R^{11}$;
$R^{11}$ is independently selected from the following:
$C_1$–$C_4$ alkyl, $C_1$–$C_4$ haloalkyl, —$NHSO_2R^{19a}$, phenyl, halogen, —$NR^{18}R^{19}$, —$OR^{19}$, —$SO_2NR^{18}R^{19}$, —$C(=O)NR^{18}R^{19}$, —$NR^{18}C(=O)R^{19}$, —$C(=O)R^{19a}$, and —$NR^{18}CO_2R^{19}$,
$R^{18}$ is independently selected from hydrogen and $C_1$–$C_4$ alkyl;
$R^{19}$ is independently selected from:
hydrogen, $C_1$–$C_4$ alkyl, phenyl, haloalkyl, an amine protecting group when $R^{19}$ is bonded to N, and a hydroxyl or carboxyl protecting group when $R^{19}$ is bonded to O; and
$R^{19a}$ is $C_1$–$C_4$ alkyl.

18. A process according to claim 17 for the preparation of a compound of formula (VI):
the process, comprising:
(1) contacting, at about –78° C. to about –33° C. for about 5 minutes to about 60 minutes, a solution of about 2.7 to about 4.4 equivalents of sodium metal dissolved in ammonia with about one equivalent of a compound of formula (I) dissolved in an aprotic solvent, selected from the group:
tetrahydrofuran, diethyl ether, ethylene glycol, dimethyl ether, t-butyl methyl ether, hexane, heptane, and cyclohexane;
(2) quenching the reaction of step (1) by addition of a suitable quenching agent, selected from the group:
ammonium chloride, ammonium bromide and ammonium iodide;
to form a compound of formula (II);
(3) isolating a compound of formula (II); and
(4) contacting a compound of formula (II) with at least one equivalent of a strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;
and at least one equivalent a compound of formula (XI) in a second aprotic solvent selected from the group:
tetrahydrofuran, diethyl ether, ethylene glycol, dimethyl ether, t-butyl methyl ether, toluene, benzene, xylene, hexane, heptane, and cyclohexane;
for a about 10 minutes to about 24 hours to effect formation of a compound of formula (IV);
(5) contacting, at about –78° C. to about –33° C. for about 5 minutes to about 60 minutes, a solution of about 2.7 to about 4.4 equivalents of sodium metal dissolved in ammonia with about one equivalent of a compound of formula (IV) in a third aprotic solvent selected from the group:
tetrahydrofuran, diethyl ether, ethylene glycol, dimethyl ether, t-butyl methyl ether, hexane, heptane, and cyclohexane;
(6) quenching the reaction of step (5) by addition of a suitable second quenching agent, selected from the group:
ammonium chloride, ammonium bromide and ammonium iodide;
to form a compound of formula (V);
(7) isolating a compound of formula (V); and
(8) contacting a compound of formula (V) with at least one equivalent of a second strong base, selected from the group:
lithium hydride, sodium hydride, potassium hydride, sodium methoxide, sodium ethoxide, lithium t-butoxide, potassium t-butoxide, sodium trimethylsilylamide, potassium trimethylsilylamide, and lithium trimethylsilylamide;
and at least one equivalent a compound of formula (XII), in a fourth aprotic solvent selected from the group:
tetrahydrofuran, diethyl ether, ethylene glycol, dimethyl ether, t-butyl methyl ether, toluene, benzene, xylene, hexane, heptane, and cyclohexane;
for about 10 minutes to about 24 hours to effect formation of a compound of formula (VI).

19. A process according to claim 18 for the preparation of a compound of formula (VI-i):

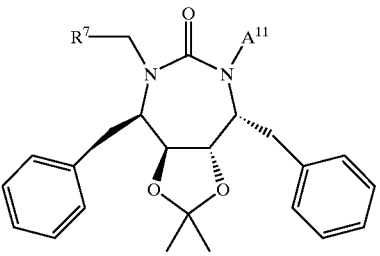

wherein:
$R^7$ is phenyl substituted with 0–2 $R^{7a}$;
$R^{7a}$ is selected from one or more of the following:
$C_1$–$C_3$ alkyl, —OH, halogen, —$CO_2R^{19}$, cyano, —$NHR^{19}$, —$OR^{19}$, —$NO_2$, —$C(=O)NHR^{19}$, —$NHC(=O)R^{19}$, —$OC(=O)NHR^{19}$, —$C(=O)R^{19}$, and —$OC(=O)R^{19}$;
$A^{11}$ is $C_1$–$C_4$ alkyl substituted with 0–2 $R^{11}$, and $R^{11}$ is $C_1$–$C_3$ alkyl, $C_2$–$C_4$ alkenyl, halogen, —$NR^{18}R^{19}$ or —$OR^{19}$;

$R^{18}$ is independently selected from hydrogen and $C_1$–$C_4$ alkyl; and $R^{19}$ is independently selected from:
hydrogen, $C_1$–$C_3$ alkyl, an amine protecting group when $R^{19}$ is bonded to N, and a hydroxyl protecting group when $R^{19}$ is bonded to O;

said process comprising:

(1) contacting, at about −33° C. for about 15 minutes to about 60 minutes, a solution of about 2.9 to about 3.5 equivalents of sodium metal dissolved in ammonia with about one equivalent of a compound of formula (I-i):

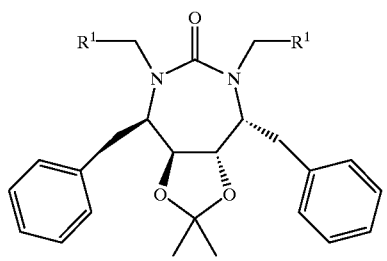

(I-i)

wherein:

$R^1$ is phenyl substituted with 0–2 $R^{1a}$;

$R^{1a}$ is selected from one or more of the following: $C_1$–$C_4$ alkyl, halogen, and —$NR^{16}R^{17}$;

$R^{16}$ is independently hydrogen or $C_1$–$C_4$ alkyl;

$R^{17}$ is independently selected from hydrogen, $C_1$–$C_4$ alkyl, and an amine protecting group;

in an aprotic solvent;

(2) quenching the reaction of step (1) by addition of ammonium chloride to form a compound of formula (II-i);

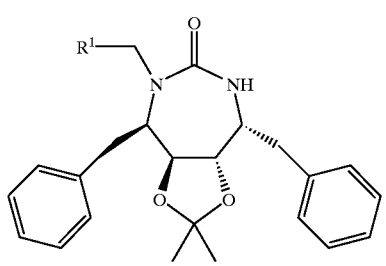

(II-i)

(3) isolating a compound of formula (II-i); and (4) contacting a compound of formula (II-i) with at least one equivalent of potassium t-butoxide or sodium hydride and at least one equivalent a compound of formula (XI):

$Z^2$—$A^{11}$ (XI)

wherein $Z^2$ is chlorine or bromine;

in a second aprotic solvent for about 15 minutes to about 24 hours to effect formation of a compound of formula (IV-i):

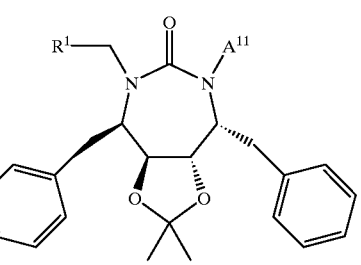

(IV-i)

(5) contacting, at about −33° C. for about 15 minutes to about 60 minutes, a solution of about 2.9 to about 3.5 equivalents of sodium metal dissolved in ammonia with about one equivalent of a compound of formula (IV-i) in a third aprotic solvent;

(6) quenching the reaction of step (5) by addition of ammonium chloride to form a compound of formula (V-i);

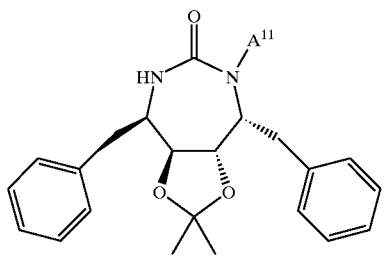

(7) isolating a compound of formula (V-i); and (8) contacting a compound of formula (V-i) with at least one equivalent of potassium t-butoxide and at least one equivalent a compound of formula (XII), $Z^3$—$CH_2$—$R^7$ (XII)

wherein $Z^3$ is chlorine or bromine;

in a fourth aprotic solvent for about 15 minutes to about 24 hours to effect formation of a compound of formula (VI-i).

20. A process according to claim 19 for the preparation of a compound of formula (VI-i), wherein the aprotic solvent is tetrahydrofuran; the second aprotic solvent is tetrahydrofuran; the third aprotic solvent is tetrahydrofuran; and the fourth aprotic solvent is tetrahydrofuran.

* * * * *